United States Patent
Canady

(10) Patent No.: US 11,737,807 B2
(45) Date of Patent: Aug. 29, 2023

(54) SYSTEM AND METHOD FOR PRE-PROGRAMMED COLD ATMOSPHERIC PLASMA

(71) Applicant: Jerome Canady Research Institute for Advanced Biological and Technological Sciences, Takoma Park, MD (US)

(72) Inventor: Jerome Canady, Lakeland, FL (US)

(73) Assignee: Jerome Canady Research Institute for Advanced, Takoma Park, MD (US)

( * ) Notice: Subject to any disclaimer, the term of this patent is extended or adjusted under 35 U.S.C. 154(b) by 407 days.

(21) Appl. No.: 16/774,421

(22) Filed: Jan. 28, 2020

(65) Prior Publication Data
US 2020/0237422 A1  Jul. 30, 2020

Related U.S. Application Data

(60) Provisional application No. 62/797,855, filed on Jan. 28, 2019.

(51) Int. Cl.
*A61B 18/00* (2006.01)
*A61B 18/04* (2006.01)

(52) U.S. Cl.
CPC .. *A61B 18/042* (2013.01); *A61B 2018/00601* (2013.01); *A61B 2018/00702* (2013.01);
(Continued)

(58) Field of Classification Search
None
See application file for complete search history.

(56) References Cited

U.S. PATENT DOCUMENTS 9,826,618 B2 * 11/2017 Eckert ................. H05H 1/2406
9,999,462 B2    6/2018 Canady et al.
(Continued)

FOREIGN PATENT DOCUMENTS

WO    2018/191265 A1    10/2018

OTHER PUBLICATIONS

Laroussi M, Kong M, Morfill G, Stolz W, editors. Plasma medicine. Cambridge; 2012.
(Continued)

*Primary Examiner* — Linda C Dvorak
*Assistant Examiner* — Nicholas S Borsch
(74) *Attorney, Agent, or Firm* — 24IP Law Group USA, PLLC; Timothy Dewitt

(57) ABSTRACT

To determine appropriate treatment doses of cold atmospheric plasma (CAP), the Canady Helios Cold Plasma Scalpel was tested across numerous cancer cell types including renal adenocarcinoma, colorectal carcinoma, pancreatic adenocarcinoma, ovarian adenocarcinoma, and esophageal adenocarcinoma. Various CAP doses were tested consisting of both high (3 L/min) and low (1 L/min) helium flow rates, several power settings, and a range of treatment times up to 5 minutes. The impact of cold plasma on the reduction of viability was consistently dose dependent, however the anti-cancer capability varied significantly between cell lines. While the lowest effective dose varied from cell line to cell line, in each case an 80-99% reduction in viability was achievable 48 hours after CAP treatment. Therefore, it is critical to select the appropriate CAP dose necessary for treating a specific cancer cell type.

11 Claims, 15 Drawing Sheets

(52) U.S. Cl.
CPC ............ *A61B 2018/00732* (2013.01); *A61B 2018/00744* (2013.01); *A61B 2018/00988* (2013.01)

(56) References Cited

U.S. PATENT DOCUMENTS

| | | | |
|---|---|---|---|
| 10,023,858 B2 | 7/2018 | Canady et al. | |
| 10,213,614 B2 | 2/2019 | Keidar et al. | |
| 10,329,535 B2 | 6/2019 | Trink et al. | |
| 10,405,913 B2 | 9/2019 | Canady et al. | |
| 2006/0009763 A1* | 1/2006 | Goble | A61B 18/042 606/49 |
| 2010/0298825 A1* | 11/2010 | Slizynski | A61B 18/1477 606/41 |
| 2015/0289923 A1* | 10/2015 | Davalos | A61B 18/1206 606/34 |
| 2015/0342663 A1* | 12/2015 | Canady | A61B 18/042 606/34 |
| 2017/0143401 A1* | 5/2017 | Woloszko | A61B 18/1206 |
| 2017/0183631 A1 | 6/2017 | Keidar et al. | |
| 2018/0103991 A1* | 4/2018 | Linhart | A61B 18/1477 |
| 2018/0271579 A1 | 9/2018 | Keidar et al. | |
| 2020/0069355 A1* | 3/2020 | Keidar | A61N 2/002 |

OTHER PUBLICATIONS

Friedman A, Friedman G. Plasma medicine. Hoboken: Wiley; 2013.
Keidar M, Beilis II. Plasma Engineering: application in aerospace, nanotechnology and bionanotechnology. Oxford: Elsevier; 2013.
Morfill GE, Kong MG, Zimmermann JL. Focus on plasma medicine. Review. New J Phys. 2009; 11:115011.
Keidar M. Plasma for cancer treatment. Plasma Source Sci Technol. 2015;24:033001.
Fridman G, Friedman G, Gutsol A, Shekhter AB, Vasilets VN, Fridman A. Applied plasma medicine. Plasma Process Polym. 2008;5:503.
Vandamme M, Robert E, Pesnel S, Barbosa E, Dozias S, Sobilo J, Lerondel S, Le Pape A, Pouvesle JM. Antitumor effect of plasma treatment on U87 Glioma Xenografts: preliminary results. Plasma Process Polym. 2010;7:264.
Keidar M, Walk R, Shashurin A, Srinivasan P, Sandler A, Dasgupta S, Ravi R, Guerrero-Preston R, Trink B. Cold plasma selectivity and the possibility of a paradigm shift in cancer therapy. Br J Cancer. 2011;105:1295-1301.
Vandamme M, Robert E, Lerondel S, Sarron V, Ries D, Dozias S, Sobilo J, Gosset D, Kieda C, Legrain B, Pouvesle J-M, Le Pape A. ROS implication in a new antitumor strategy based on non-thermal plasma. Int J Cancer. 2011;130:2185.
Metelmann HR. What kind of impact is possible by plasma-jet in head and neck cancer?, The 2nd International Workshop on Plasma for Cancer Treatment, Nagoya, Japan, Mar. 2015.
Canady J. "Development and clinical application of hybrid and cold atmospheric plasma combined with systemic chemotherapy and selective 3D conformal radiation therapy: A novel approach to the treatment of peritoneal metastases from colorectal cancer." The 2nd International Workshop on Plasma for Cancer Treatment, Nagoya, Japan, Mar. 2015.
Metelmann HR, Nedrelow DS, Seebauer C, Schuster M, von Woedtke T, Weltmann K-D, Kindler S, Metelmann PH, Finkelstein SE, Von Hoff DD, Podmelle F. Head and neck cancer treatment and physical plasma. Clin Plasma Med. 2015;3:17-23.
Yan D, Sherman J H and Keidar M, "Cold atmospheric plasma, a novel promising anti-cancer treatment modality," Oncotarget. 8 15977-15995 (2017).
Hirst A M, Frame F M, Arya M, Maitland N J and O'Connell D, "Low temperature plasmas as emerging cancer therapeutics: the state of play and thoughts for the future," Tumor Biol. 37 7021-7031 (2016).

Vandamme M, Robert E, Dozias S, Sobilo J, Lerondel S, Le Pape A and Pouvesle J-M, "Response of human glioma U87 xenografted on mice to non thermal plasma treatment," Plasma Med. 1 27-43 (2011).
Brulle L, Vandamme M, Ries D, Martel E, Robert E, Lerondel S, Trichet V, Richard S, Pouvesle J M and Le Pape A, "Effects of a Non thermal plasma treatment alone or in combination with gemcitabine in a MIA PaCa2-lucorthotopic pancreatic carcinoma model," PLoS One. 7 e52653 (2012).
Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," Plasma Process. Polym. 12 1400-1409 (2015).
Turhal, N., "Two cases of advanced renal cell cancer with prolonged survival of 8 and 12 years," Jpn J Clin Oncol 2002, 32, 152-153.
Dabestani, S.; Beisland, C.; Stewart, G.D.; Bensalah, K.; Gudmundsson, E.; Lam, T.B.; Gietzmann, W.; Zakikhani, P.; Marconi, L.; Fernandez-Pello, S., et al., "Long-term outcomes of follow-up for initially localised clear cell renal cell carcinoma: Recur database analysis," Eur Urol Focus 2018.
Wille-Jorgensen, P.; Syk, I.; Smedh, K.; Laurberg, S.; Nielsen, D.T.; Petersen, S.H.; Renehan, A.G.; Horvath-Puho, E.; Pahlman, L.; Sorensen, H.T., et al., "Effect of more vs less frequent follow-up testing on overall and colorectal cancer-specific mortality in patients with stage ii or iii colorectal cancer: The colofol randomized clinical trial," JAMA 2018, 319, 2095-2103.
Benzel, J.; Fendrich, V., "Chemoprevention and treatment of pancreatic cancer: Update and review of the literature," Digestion 2018, 97, 275-287.
Nakayama, Y.; Sugimoto, M.; Gotohda, N.; Konishi, M.; Takahashi, S., "Efficacy of completion pancreatectomy for recurrence of adenocarcinoma in the remnant pancreas," J Surg Res 2018, 221, 15-23.
Conroy, T.; Desseigne, F.; Ychou, M.; Bouche, O.; Guimbaud, R.; Becouarn, Y.; Adenis, A.; Raoul, J.L.; Gourgou-Bourgade, S.; de la Fouchardiere, C., et al., "Folfirinox versus gemcitabine for metastatic pancreatic cancer," N Engl J Med 2011, 364, 1817-1825.
Torre, L.A.; Trabert, B.; DeSantis, C.E.; Miller, K.D.; Samimi, G.; Runowicz, C.D.; Gaudet, M.M.; Jemal, A.; Siegel, R.L, "Ovarian cancer statistics 2018," CA Cancer J Clin 2018.
Hou, M.M.; Chen, Y.; Wu, Y.K.; Xi, M.R., "Pathological characteristics and prognosis of 664 patients with epithelial ovarian cancer: A retrospective analysis," Sichuan Da Xue Xue Bao Yi Xue Ban 2014, 45, 859-862, 875.
Visser, E.; Edholm, D.; Smithers, B.M.; Thomson, I.G.; Burmeister, B.H.; Walpole, E.T.; Gotley, D.C.; Joubert, W.L.; Atkinson, V.; Mai, T., et al., "Neoadjuvant chemotherapy or chemoradiotherapy for adenocarcinoma of the esophagus," J Surg Oncol 2018.
Xi, M.; Yang, Y.; Zhang, L.; Yang, H.; Merrell, K.W.; Hallemeier, C.L.; Shen, R.K.; Haddock, M.G.; Hofstetter, W.L.; Maru, D.M., et al., "Multi-institutional analysis of recurrence and survival after neoadjuvant chemoradiotherapy of esophageal cancer: Impact of histology on recurrence patterns and outcomes," Ann Surg 2018.
Yan, D.; Talbot, A.; Nourmohammadi, N.; Cheng, X.; Canady, J.; Sherman, J.; Keidar, M., "Principles of using cold atmospheric plasma stimulated media for cancer treatment," Sci Rep 2015, 5, 18339.
Naciri, M.; Dowling, D.; Al-Rubeai, M., "Differential sensitivity of mammalian cell lines to non-thermal atmospheric plasma," Plasma Processes and Polymers 2014, 11, 391-400.
Ma, Y.; Ha, C.S.; Hwang, S.W.; Lee, H.J.; Kim, G.C.; Lee, K.W.; Song, K., "Non-thermal atmospheric pressure plasma preferentially induces apoptosis in p53-mutated cancer cells by activating ros stress-response pathways," PLoS One 2014, 9, e91947.
Dayun Yan, Jonathan H. Sherman, Jerome Canady, Barry Trink, Michael Keidar, "The cellular ros-scavenging function, a key factor determining the specific vulnerability of cancer cells to cold atmospheric plasma in vitro," arXiv.org; arXiv:1711.09015: 2017; vol. arXiv:1711.09015.

(56) References Cited

OTHER PUBLICATIONS

Lee, H.J.; Shon, C.H.; Kim, Y.S.; Kim, S.; Kim, G.C.; Kong, M.G., "Degradation of adhesion molecules of g361 melanoma cells by a non-thermal atmospheric pressure microplasma," New Journal of Physics 2009, 11.

Schmidt, A.; Bekeschus, S.; von Woedtke, T.; Hasse, S., "Cell migration and adhesion of a human melanoma cell line is decreased by cold plasma treatment," Clinical Plasma Medicine 2015, 3, 24-31.

Shi, X.-M.; Zhang, G.-J.; Chang, Z.-S.; Wu, X.-L.; Liao, W.-L.; Li, N., "Viability reduction of melanoma cells by plasma jet via inducing g1/s and g2/m cell cycle arrest and cell apoptosis," IEEE Transactions on Plasma Science 2014, 42, 1640-1647.

Chang, J.W.; Kang, S.U.; Shin, Y.S.; Kim, K.I.; Seo, S.J.; Yang, S.S.; Lee, J.S.; Moon, E.; Baek, S.J.; Lee, K., et al., "Non-thermal atmospheric pressure plasma induces apoptosis in oral cavity squamous cell carcinoma: Involvement of DNA damage-triggering sub-g(1) arrest via the atm/p53 pathway," Arch Biochem Biophys 2014, 545, 133-140.

Gherardi, M.; Turrini, E.; Laurita, R.; De Gianni, E.; Ferruzzi, L.; Liguori, A.; Stancampiano, A.; Colombo, V.; Fimognari, C., "Atmospheric nonequilibrium plasma promotes cell death and cell-cycle arrest in a lymphoma cell line," Plasma Processes and Polymers 2015, 12, 1354-1363.

Adachi, T.; Tanaka, H.; Nonomura, S.; Hara, H.; Kondo, S.; Hori, M., "Plasma-activated medium induces a549 cell injury via a spiral apoptotic cascade involving the mitochondrial-nuclear network," Free Radic Biol Med 2015, 79, 28-44.

Ahn, H.J.; Kim, K.I.; Kim, G.; Moon, E.; Yang, S.S.; Lee, J.S., "Atmospheric-pressure plasma jet induces apoptosis involving mitochondria via generation of free radicals," PLoS One 2011, 6, e28154.

Kim, S.J.; Chung, T.H.; Bae, S.H.; Leem, S.H., "Induction of apoptosis in human breast cancer cells by a pulsed atmospheric pressure plasma jet," Applied Physics Letters 2010, 97.

Nuccitelli, R.; Chen, X.; Pakhomov, A.G.; Baldwin, W.H.; Sheikh, S.; Pomicter, J.L.; Ren, W.; Osgood, C.; Swanson, R.J.; Kolb, J.F., et al., "A new pulsed electric field therapy for melanoma disrupts the tumor's blood supply and causes complete remission without recurrence," Int J Cancer 2009, 125, 438-445.

Chung, W.H., "Mechanisms of a novel anticancer therapeutic strategy involving atmospheric pressure plasma-mediated apoptosis and DNA strand break formation," Arch Pharm Res 2016, 39, 1-9.

\* cited by examiner

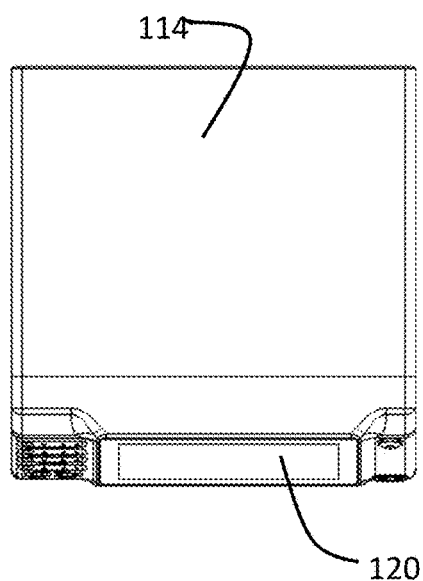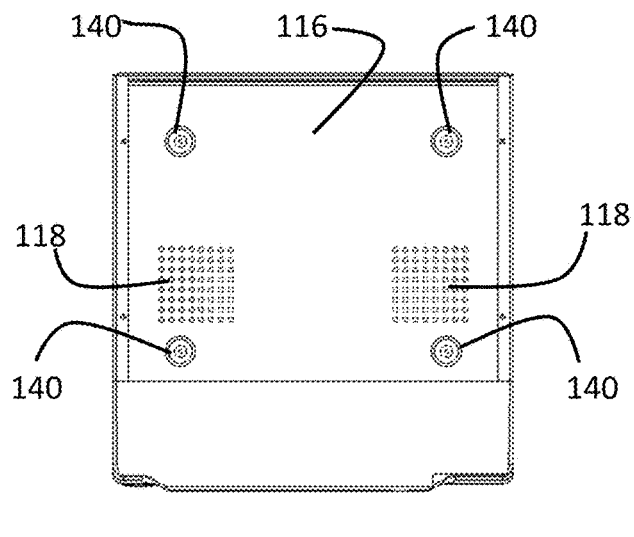
FIG. 1F
FIG. 1G

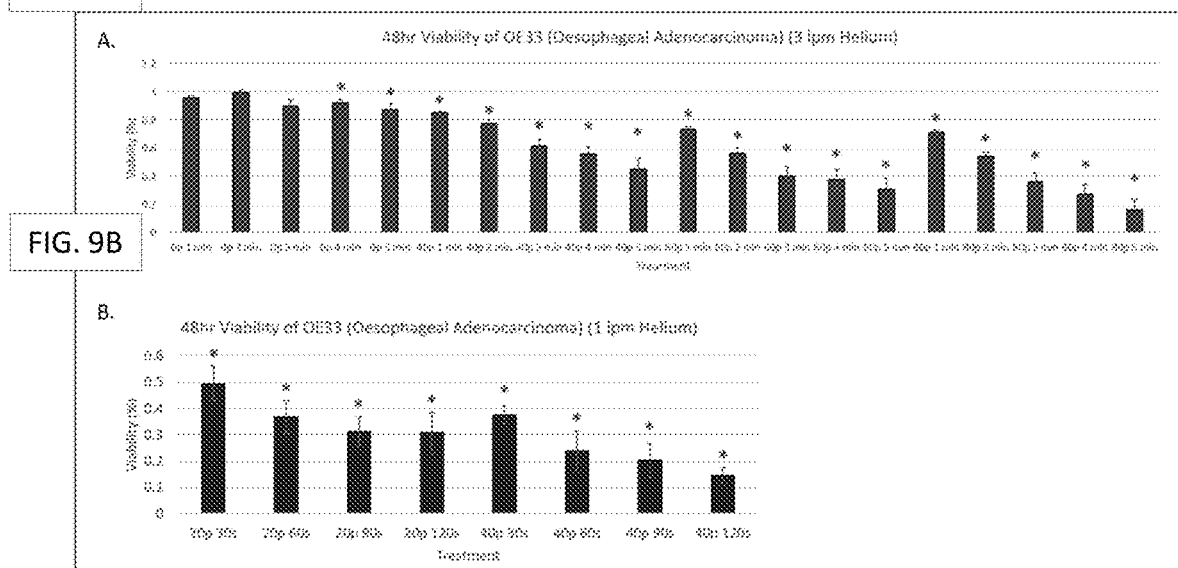
FIG. 9A
FIG. 9B
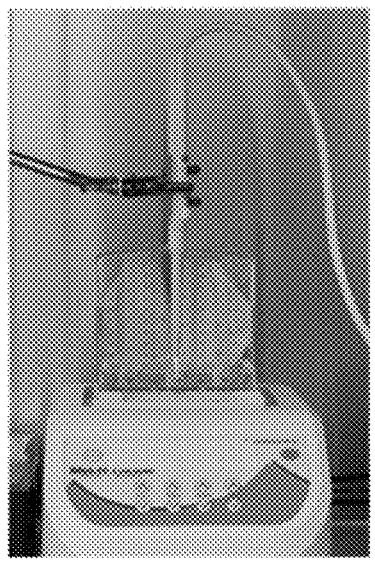
FIG. 10A
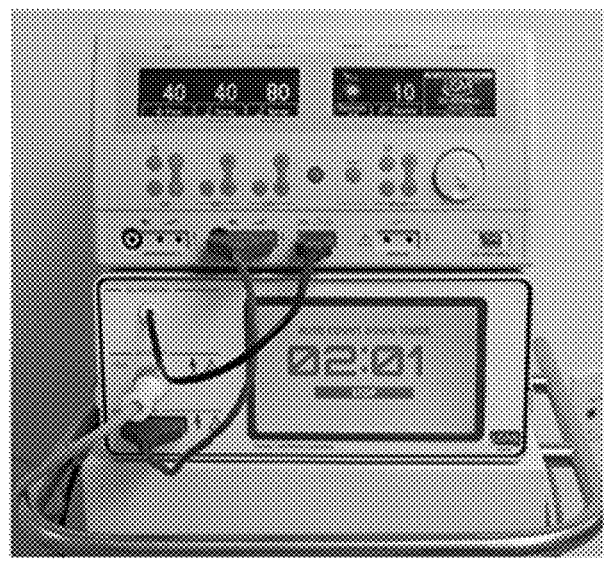
FIG. 10B

| Cell Name | Cell Type | Power | Flow Rate | Time |
|---|---|---|---|---|
| 769-P | Renal adenocarcinoma | 40W | 1 L/min | 120s |
| HCT-116 | Colorectal carcinoma | 20W | 1L/min | 120s |
| SK-OV-3 | Ovarian adenocarcinoma | 40W | 1 L/min | 120s |
| BxPC-3 | Pancreatic adenocarcinoma | 40W | 1L/min | 120s |
| OE33 | Esophageal adenocarcinoma | 40W | 1 L/min | 120s |

FIG. 12

SYSTEM AND METHOD FOR PRE-PROGRAMMED COLD ATMOSPHERIC PLASMA

CROSS-REFERENCE TO RELATED APPLICATIONS

The present application claims the benefit of the filing date of U.S. Provisional Patent Application Ser. No. 62/797,855 filed by the present inventors on Jan. 28, 2019.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for using cold atmospheric plasma to treat cancer.

Brief Description of the Related Art

Plasma medicine has qualified as a new scientific field after intense research effort in low-temperature or cold atmospheric plasma applications. See, Laroussi M, Kong M, Morfill G, Stolz W, editors. Plasma medicine. Cambridge; 2012; Friedman A, Friedman G. Plasma medicine. Hoboken: Wiley; 2013; and Keidar M, Beilis II. Plasma Engineering: application in aerospace, nanotechnology and bionanotechnology. Oxford: Elsevier; 2013. It is known that cold atmospheric plasmas (CAP) produce various chemically reactive species including reactive oxygen species (ROS) and reactive nitrogen species (RNS). CAP is a cocktail containing ROS and RNS in combination with transient electric fields, UV and charged species.

CAP has already been proven to be effective in wound healing, skin diseases, hospital hygiene, sterilization, antifungal treatments, dental care, and cosmetics targeted cell/tissue removal. See, Morfill G E, Kong M G, Zimmermann J L. Focus on plasma medicine. Review. New J Phys. 2009; 11:115011; Keidar M. Plasma for cancer treatment. Plasma Source Sci Technol. 2015; 24:033001; and Fridman G, Friedman G, Gutsol A, Shekhter A B, Vasilets V N, Fridman A. Applied plasma medicine. Plasma Process Polym. 2008; 5:503. One of the most recent applications of CAP is in cancer therapy. See, Vandamme M, Robert E, Pesnel S, Barbosa E, Dozias S, Sobilo J, Lerondel S, Le Pape A, Pouvesle J M. Antitumor effect of plasma treatment on U87 Glioma Xenografts: preliminary results. Plasma Process Polym. 2010; 7:264; Keidar M, Walk R, Shashurin A, Srinivasan P, Sandler A, Dasgupta S, Ravi R, Guerrero-Preston R, Trink B. Cold plasma selectivity and the possibility of a paradigm shift in cancer therapy. Br J Cancer. 2011; 105:1295; and Vandamme M, Robert E, Lerondel S, Sarron V, Ries D, Dozias S, Sobilo J, Gosset D, Kieda C, Legrain B, Pouvesle J-M, Le Pape A. ROS implication in a new antitumor strategy based on non-thermal plasma. Int J Cancer. 2011; 130:2185. Multiple studies have convincingly demonstrated that the CAP treatment leads to selective eradication of cancer cells in vitro and reduction of tumor size in vivo. While most studies were done in vitro, some work was done in vivo. Recently, clinical cases of CAP application in cancer therapy were presented at the 2nd International Workshop on Plasma for Cancer Therapy in Nagoya (Japan) and one of these studies involving 12 patients afflicted with advanced squamous cell carcinoma of the head and neck has been documented in a recent paper. See, Metelmann H R. What kind of impact is possible by plasma-jet in head and neck cancer?", The 2nd International Workshop on Plasma for Cancer Treatment, Nagoya, Japan, March, 2015; Canady J. "Development and clinical application of hybrid and cold atmospheric plasma combined with systemic chemotherapy and selective 3D conformal radiation therapy: A novel approach to the treatment of peritoneal metastases from colorectal cancer." The $2^{nd}$ International Workshop on Plasma for Cancer Treatment, Nagoya, Japan, March 2015; and Metelmann H R, Nedrelow D S, Seebauer C, Schuster M, von Woedtke T, Weltmann K-D, Kindler S, Metelmann P H, Finkelstein S E, Von Hoff D D, Podmelle F. Head and neck cancer treatment and physical plasma. Clin Plasma Med. 2015; 3:17-23.

As a near-room temperature ionized gas, cold atmospheric plasma (CAP) has demonstrated its promising capability in cancer treatment by causing the selective death of cancer cells in vitro. See, Yan D, Sherman J H and Keidar M, "Cold atmospheric plasma, a novel promising anti-cancer treatment modality," Oncotarget. 8 15977-15995 (2017); Keidar M, "Plasma for cancer treatment," Plasma Sources Sci. Technol. 24 33001 (2015); Hirst A M, Frame F M, Arya M, Maitland N J and O'Connell D, "Low temperature plasmas as emerging cancer therapeutics: the state of play and thoughts for the future," Tumor Biol. 37 7021-7031 (2016). The CAP treatment on several subcutaneous xenograft tumors and melanoma in mice has also demonstrated its potential clinical application. See, Keidar M, Walk R, Shashurin A, Srinivasan P, Sandler A, Dasgupta S, Ravi R, Guerrero-Preston R and Trink B, "Cold plasma selectivity and the possibility of a paradigm shift in cancer therapy," Br. J. Cancer. 105 1295-301 (2011); Vandamme M, Robert E, Dozias S, Sobilo J, Lerondel S, Le Pape A and Pouvesle J-M, "Response of human glioma U87 xenografted on mice to non thermal plasma treatment," Plasma Med. 1 27-43 (2011); Brulle L, Vandamme M, Ries D, Martel E, Robert E, Lerondel S, Trichet V, Richard S, Pouvesle J M and Le Pape A, "Effects of a Non thermal plasma treatment alone or in combination with gemcitabine in a MIA PaCa2-luc orthotopic pancreatic carcinoma model," PLoS One. 7 e52653 (2012); and Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," Plasma Process. Polym. 12 1400-1409 (2015).

Several different systems and methods for performing Cold Atmospheric Plasma (CAP) treatment have been disclosed. For example, U.S. Pat. No. 10,213,614 discloses a two-electrode system for CAP treatement.

Another exemplary Cold Atmospheric Plasma system is disclosed in U.S. Pat. No.9,999,462. The disclosed system has two units, namely a Conversion Unit (CU) and a Cold Plasma Probe (CPP). The Conversion Unit is connected to an electrosurgical generator (ESU) output and converts the ESU signal to a signal appropriate for performing cold atmospheric plasma procedures. The Cold Plasma Probe is connected to the Conversion Unit output. At the end of the Cold Plasma Probe cold plasma is produced and is thermally harmless to living tissue, i.e., it cannot cause burns to the tissue. This cold plasma, however, is deadly for cancer cells while leaving normal cells unaffected. The disclosed Cold Plasma Conversion Unit is unique in that it utilizes a high voltage transformer to up-convert the voltage (1.5-50 kV), down-convert the frequency (<300 kHz), and down-convert the power (<30 W) of the high-voltage output from an electrosurgical unit (U.S. Pat. No. 9,999,462).

Malignant solid tumors are characterized by high recurrence rates and low 5-year survival rates. Stage IV renal adenocarcinoma presents an extremely low 5-year survival rate of 0-10% (see, Turhal, N., "Two cases of advanced renal cell cancer with prolonged survival of 8 and 12 years," *Jpn J Clin Oncol* 2002, 32, 152-153), while the recurrence rate may be as high as 23%. See, Dabestani, S.; Beisland, C.; Stewart, G. D.; Bensalah, K.; Gudmundsson, E.; Lam, T. B.; Gietzmann, W.; Zakikhani, P.; Marconi, L.; Fernandez-Pello, S., et al., "Long-term outcomes of follow-up for initially localised clear cell renal cell carcinoma: Recur database analysis," *Eur Urol Focus* 2018. While the recurrence rate of colorectal carcinoma is similar to that of renal adenocarcinoma at 19.4% to 21.6%, the 5-year survival rate is significantly higher at 88.6% to 89.4% [3]. See, Wille-Jorgensen, P.; Syk, I.; Smedh, K.; Laurberg, S.; Nielsen, D. T.; Petersen, S. H.; Renehan, A. G.; Horvath-Puho, E.; Pahlman, L.; Sorensen, H. T., et al., "Effect of more vs less frequent follow-up testing on overall and colorectal cancer-specific mortality in patients with stage ii or iii colorectal cancer: The colofol randomized clinical trial," *JAMA* 2018, 319, 2095-2103. Pancreatic ductal adenocarcinoma has an extremely low survival rate of 10% to 28% (Benzel, J.; Fendrich, V., "Chemoprevention and treatment of pancreatic cancer: Update and review of the literature," *Digestion* 2018, 97, 275-287) after one year due to a very high recurrence rate of 65.5%. See, Nakayama, Y.; Sugimoto, M.; Gotohda, N.; Konishi, M.; Takahashi, S., "Efficacy of completion pancreatectomy for recurrence of adenocarcinoma in the remnant pancreas," *J Surg Res* 2018, 221, 15-23. The resulting 5-year survival rate is dismal at 6% in the United States and Europe. See, Conroy, T.; Desseigne, F.; Ychou, M.; Bouche, O.; Guimbaud, R.; Becouarn, Y.; Adenis, A.; Raoul, J. L.; Gourgou-Bourgade, S.; de la Fouchardiere, C., et al., "Folfirinox versus gemcitabine for metastatic pancreatic cancer," *N Engl J Med* 2011, 364, 1817-1825. Serous epithelial ovarian carcinoma has a very low 5-year survival rate of 42% for stage III and 26% for stage IV (see, Torre, L. A.; Trabert, B.; DeSantis, C. E.; Miller, K. D.; Samimi, G.; Runowicz, C. D.; Gaudet, M. M.; Jemal, A.; Siegel, R. L, "Ovarian cancer statistics 2018," *CA Cancer J Clin* 2018) with a 19% recurrence rate (Hou, M. M.; Chen, Y.; Wu, Y. K.; Xi, M. R., "Pathological characteristics and prognosis of 664 patients with epithelial ovarian cancer: A retrospective analysis," Sichuan Da Xue Xue Bao Yi Xue Ban 2014, 45, 859-862, 875). Esophageal adenocarcinoma represents a similarly low 5-year survival rate of 33% to 44% (see, Visser, E.; Edholm, D.; Smithers, B. M.; Thomson, I. G.; Burmeister, B. H.; Walpole, E. T.; Gotley, D. C.; Joubert, W. L.; Atkinson, V.; Mai, T., et al., "Neoadjuvant chemotherapy or chemoradiotherapy for adenocarcinoma of the esophagus," *J Surg Oncol* 2018), depending on the treatment used, and can result in a recurrence rate as high as 43.2% (see, Xi, M.; Yang, Y.; Zhang, L.; Yang, H.; Merrell, K. W.; Hallemeier, C. L.; Shen, R. K.; Haddock, M. G.; Hofstetter, W. L.; Maru, D. M., et al., "Multi-institutional analysis of recurrence and survival after neoadjuvant chemoradiotherapy of esophageal cancer: Impact of histology on recurrence patterns and outcomes," *Ann Surg* 2018).

The unfortunately common recurrence rate of malignant solid tumors represents a unique opportunity for cold atmospheric plasma (CAP) treatment. CAP can be used to treat the margins following tumor removal, and in doing so has the potential to remove residual cancer cells and prevent recurrence. An important step to make this a reality is to determine the correct dose of CAP to significantly reduce tumor cell viability. It has been reported that various cell lines react differently to CAP treatment [11-14]. See, Yan, D.; Talbot, A.; Nourmohammadi, N.; Cheng, X.; Canady, J.; Sherman, J.; Keidar, M., "Principles of using cold atmospheric plasma stimulated media for cancer treatment," *Sci Rep* 2015, 5, 18339; Naciri, M.; Dowling, D.; Al-Rubeai, M., "Differential sensitivity of mammalian cell lines to non-thermal atmospheric plasma," *Plasma Processes and Polymers* 2014, 11, 391-400; and Ma, Y.; Ha, C. S.; Hwang, S. W.; Lee, H. J.; Kim, G. C.; Lee, K. W.; Song, K., "Non-thermal atmospheric pressure plasma preferentially induces apoptosis in p53-mutated cancer cells by activating ros stress-response pathways," *PLoS One* 2014, 9, e91947. Dayun Yan, Jonathan H. Sherman, Jerome Canady, Barry Trink, Michael Keidar, "The cellular ros-scavenging function, a key factor determining the specific vulnerability of cancer cells to cold atmospheric plasma in vitro," arXiv.org; arXiv:1711.09015: 2017; Vol. arXiv:1711.09015. Yan et al. studied the reactive species consumption speed of glioblastoma U87 and breast cancers MDA-MB-231 and MCF-7, and discovered that the cancer cells that could absorb or eliminate the effective species in the media faster (glioblastoma) would be more resistant to plasma-activated medium than both breast cancers. Their results also demonstrate a wide range of effects on cell viability depending on cell type and treatment time used. Naciri et al. also reported that plasma sensitivity closely correlates with proliferation rates by measuring ATP levels of 3 cancer cell types including Chinese hamster ovary cells, osteoblast, and colon adenocarcinoma. By testing 8 cancerous cell lines, Ma et al. claimed that p53-deficient cancer cells are more sensitive to CAP treatment due to the lack of p53-dependent cell cycle delay at G1. Therefore, the combinations of power settings and treatment times are critical for the correct dosage of cell line-dependent CAP treatment establishment.

The mechanism of anti-cancer capacity of CAP has been increasingly understood. Several theories have been proposed, including decrease of cell adhesion, interruption of cell cycle, induction of apoptosis and DNA fragmentation. For decrease of cell adhesion, see Lee, H. J.; Shon, C. H.; Kim, Y. S.; Kim, S.; Kim, G. C.; Kong, M. G., "Degradation of adhesion molecules of g361 melanoma cells by a non-thermal atmospheric pressure microplasma," *New Journal of Physics* 2009, 11 and Schmidt, A.; Bekeschus, S.; von Woedtke, T.; Hasse, S., "Cell migration and adhesion of a human melanoma cell line is decreased by cold plasma treatment," *Clinical Plasma Medicine* 2015, 3, 24-31. For interruption of cell cycle, see, Shi, X.-M.; Zhang, G.-J.; Chang, Z.-S.; Wu, X.-L.; Liao, W.-L.; Li, N., "Viability reduction of melanoma cells by plasma jet via inducing g1/s and g2/m cell cycle arrest and cell apoptosis," *IEEE Transactions on Plasma Science* 2014, 42, 1640-1647; Chang, J. W.; Kang, S. U.; Shin, Y. S.; Kim, K. I.; Seo, S. J.; Yang, S. S.; Lee, J. S.; Moon, E.; Baek, S. J.; Lee, K., et al., "Non-thermal atmospheric pressure plasma induces apoptosis in oral cavity squamous cell carcinoma: Involvement of DNA-damage-triggering sub-g(1) arrest via the atm/p53 pathway," *Arch Biochem Biophys* 2014, 545, 133-140, and Gherardi, M.; Turrini, E.; Laurita, R.; De Gianni, E.; Ferruzzi, L.; Liguori, A.; Stancampiano, A.; Colombo, V.; Fimognari, C., "Atmospheric non-equilibrium plasma promotes cell death and cell-cycle arrest in a lymphoma cell line," *Plasma Processes and Polymers* 2015, 12, 1354-1363

For induction of apoptosis, see Adachi, T.; Tanaka, H.; Nonomura, S.; Hara, H.; Kondo, S.; Hori, M., "Plasma-activated medium induces a549 cell injury via a spiral apoptotic cascade involving the mitochondrial-nuclear network," *Free Radic Biol Med* 2015, 79, 28-44; Ahn, H. J.; Kim, K. I.; Kim, G.; Moon, E.; Yang, S. S.; Lee, J. S., "Atmospheric-pressure plasma jet induces apoptosis involving mitochondria via generation of free radicals," *PLoS One* 2011, 6, e28154; and Kim, S. J.; Chung, T. H.; Bae, S. H.; Leem, S. H., "Induction of apoptosis in human breast cancer cells by a pulsed atmospheric pressure plasma jet," Applied Physics Letters 2010, 97; and Keidar, M.; Walk, R.; Shashurin, A.; Srinivasan, P.; Sandler, A.; Dasgupta, S.; Ravi, R.; Guerrero-Preston, R.; Trink, B., "Cold plasma selectivity and the possibility of a paradigm shift in cancer therapy," *Br J Cancer* 2011, 105, 1295-1301.

For DNA fragmentation, see Nuccitelli, R.; Chen, X.; Pakhomov, A. G.; Baldwin, W. H.; Sheikh, S.; Pomicter, J. L.; Ren, W.; Osgood, C.; Swanson, R. J.; Kolb, J. F., et al., "A new pulsed electric field therapy for melanoma disrupts the tumor's blood supply and causes complete remission without recurrence," *Int J Cancer* 2009, 125, 438-445. However, it is not yet clear whether CAP generated reactive species are crucial for apoptosis and its associated DNA strand break or whether plasma-induced direct DNA damage provokes cell cycle checkpoint signaling that leads to apoptosis. Chung, W. H., "Mechanisms of a novel anticancer therapeutic strategy involving atmospheric pressure plasma-mediated apoptosis and DNA strand break formation," *Arch Pharm Res* 2016, 39, 1-9.

SUMMARY OF THE INVENTION

In a preferred embodiment, the present invention is a pre-programmed system for performing cold atmospheric plasma treatment on target tissue. The system has an RF energy source, a low frequency conversion unit, a gas control device, a processor configured to control the RF energy module, the LF conversion module and the gas control module, a display, graphical user interface displayed on the display for controlling cold atmospheric plasma procedures, a data storage unit or memory; and a database stored in the data storage unit or memory, the database comprising cell lines identifying data and cold atmospheric plasma settings associated with the cell line identifying data. The graphical user interface has input means for a surgeon to enter cell line identifier data and in response to the entry of cell line identifier data the electrosurgical generator automatically accesses the database in the data storage or memory and adopts cold atmospheric plasma settings associated with the entered cell line identifier data in the database and displays the adopted cold atmospheric plasma settings on the display. The RF energy source may be a monopolar electrosurgical generator, gas control module and LF conversion unit may be separate devices or may be within an integrated cold atmospheric plasma generator or a variation in which the RF energy and conversion unit are in an integrated unit while the gas control module is in a separate device. In a preferred embodiment, the processor is in the integrated cold atmospheric plasma generator. The data storage unit or memory may be within the integrated cold atmospheric plasma generator or may be external thereof. The display comprises a touchscreen, for example, on a tablet computer. The data storage or memory may be a memory in the processor. The cold atmospheric plasma settings may comprise at least two of power, flow rate and time.

In another preferred embodiment, the present invention is a method for applying cold atmospheric plasma treatment on target tissue. The method comprises the steps of selecting through a graphical user interface on a display a particular cancer cell line associated with the target tissue, retrieving in response to the selecting, with a computing device connected to the display, settings data from a database of cell line data and associated settings data in a storage, applying, with the computing device, the retrieved settings data to a cold atmospheric plasma system, and treating cancer tissue with cold atmospheric plasma at the retrieved settings. The method may further comprise displaying the retrieved settings on a display.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 1F is a top view of a preferred embodiment of a gas-enhanced electrosurgical generator.

FIG. 1G is a bottom view of a preferred embodiment of a gas-enhanced electrosurgical generator.

FIGS. 9A and 9B illustrates reduction of viability of OE33 following CAP treatment. CAP treatment of OE33 significantly reduces viability at all doses tested.

FIGS. 10A and 10B illustrate an experimental setup for solid tumor treatment with cold atmospheric plasma. FIG. 10A illustrates cells cultured in a 12-well plate, treated using a Canady Helios Plasma Scalpel at 3 L/min. FIG. 10B illustrates an electrosurgical generator connected to a Cold Plasma Conversion Unit.

FIG. 12 is a diagram of an exemplary CAP database in accordance with a preferred embodiment of the present invention.

DETAILED DESCRIPTION OF THE PREFERRED EMBODIMENTS

As shown in the experiments discussed below, various cancer cell line can be tested to provide a rough prediction of which cells lines are susceptible to treatment with CAP and further, the various cancer cell lines can be tested at varying settings or dosages of the CAP treatment on provide an estimate of which CAP treatment settings or dosages will provide the greatest effect on particular cancer cell lines. In a preferred embodiment of the present invention, the results of such testing are used to generate a database of cancer cell lines with associated predicted optimum settings or dosage data and optionally effectiveness data. This database can be stored in memory or other storage in a CAP capable electrosurgical system or can be in an external storage, for example, accessible through a server or cloud computing system, that can be accessed by a CAP capable electrosurgical system. The database effectively pre-programs the system to treat a particular cancer cell line with CAP at particular settings. The CAP capable electrosurgical system may have a graphical user interface that allows a user to enter an identifier for a particular cancer cell line into the user interface and thereby have the CAP-enabled electrosurgical system automatically select the predicted optimum settings or dosage for that particular cancer cell line. The user can then perform a CAP treatment of target cancer cells at those predicted optimum settings.

Figure 11:
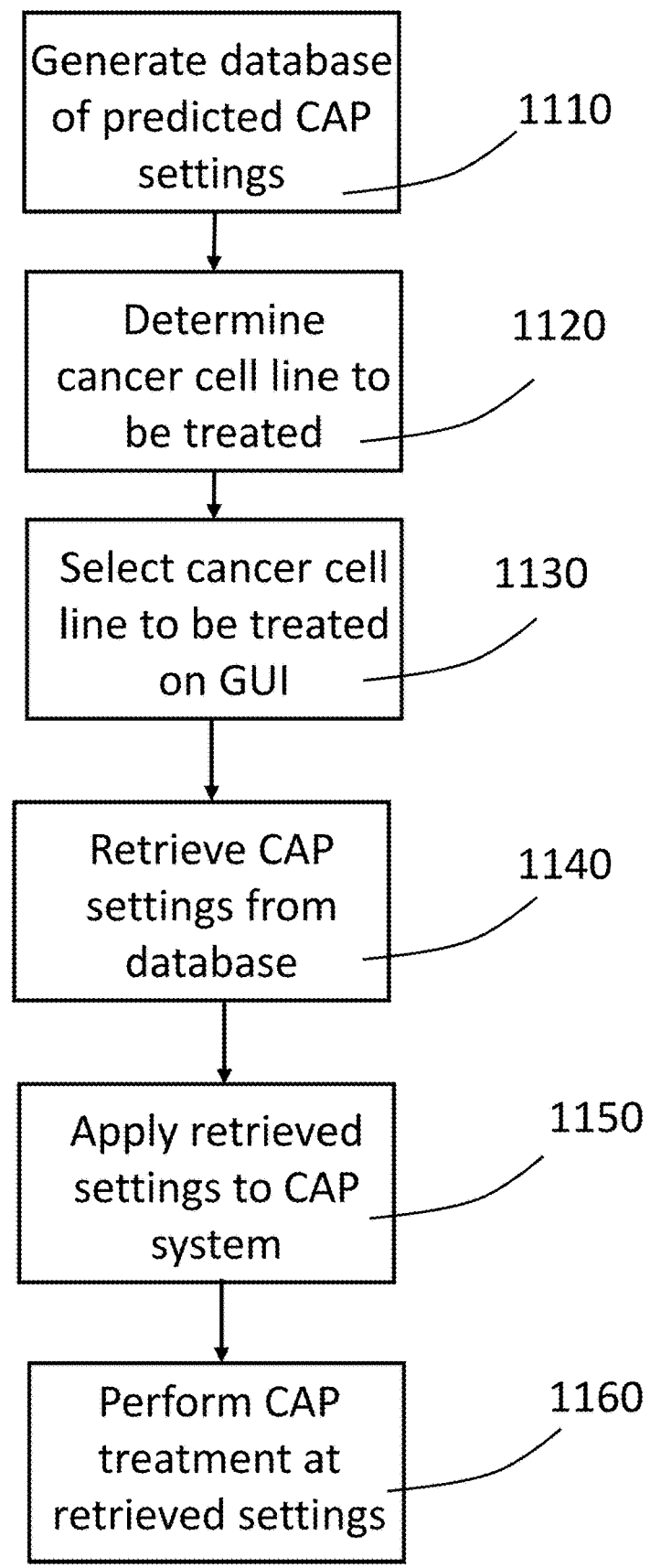
FIG. 11 is a flow chart of a method for performing CAP treatment in accordance with a preferred embodiment of the present invention.

Thus, as shown in FIG. 11, a method can be performed in which a database of cancer cell lines and associated CAP treatment data is generated and stored (step 1110). Additional cancer cell line data and associate settings or dosage data can be added to the database as new cell lines are tested and new data is developed. A user performing a CAP treatment determines the particular cancer cell line to be treated (step 1120) and then enters an identifier associated with a particular cancer cell line into a graphical user interface on a CAP capable electrosurgical system (step 1130). The CAP capable electrosurgical system then accesses the stored database to retrieve CAP setting or dosages associated with the ID entered into the graphical user interface (step 1140). The phrase "enter an identifier" used herein can mean any data entry or selection by the user that provides the graphical user interface with sufficient information to retrieve data from the database for a particular cell line. This could be selection from a list or menu, entry of an identifier through a physical or virtual keyboard associated with the system, scanning of a bar code, or any other means. Further, the graphical user interface and associated display do not need to physically be in the CAP capable generator but instead may be on external devices such as a tablet computing device that is in communication with the CAP enabled electrosurgical generator. The retrieved CAP settings are then applied to the CAP system (step 1150). The user then can treat the target tissue with CAP at the preferred settings (step 1160).

A preferred embodiment of a CAP enable generator is described with reference to the drawings. A gas-enhanced electrosurgical generator 100 in accordance with a preferred embodiment of the present invention is shown in FIGS. 1A-1G. The gas-enhanced generator has a housing 110 made of a sturdy material such as plastic or metal similar to materials used for housings of conventional electrosurgical generators. The housing 110 has a removable cover 114. The housing 110 and cover 114 have means, such as screws 119, tongue and groove, or other structure for removably securing the cover to the housing. The cover 114 may comprise just the top of the housing or multiple sides, such as the top, right side and left side, of the housing 110. The housing 110 may have a plurality of feet or legs 140 attached to the bottom of the housing. The bottom 116 of the housing 110 may have a plurality of vents 118 for venting from the interior of the gas-enhanced generator.

On the face 112 of the housing 114 there is a touch-screen display 120 and a plurality of connectors 132, 134 for connecting various accessories to the generator, such as an argon plasma probe, a hybrid plasma probe, a cold atmospheric plasma probe, or any other electrosurgical attachment. There is a gas connector 136 for connecting, for example, a $CO_2$ supply for insufflating an abdomen. The face 112 of the housing 110 is at an angle other than 90 degrees with respect to the top and bottom of the housing 110 to provide for easier viewing and use of the touch screen display 120 by a user.

Figure 1A:
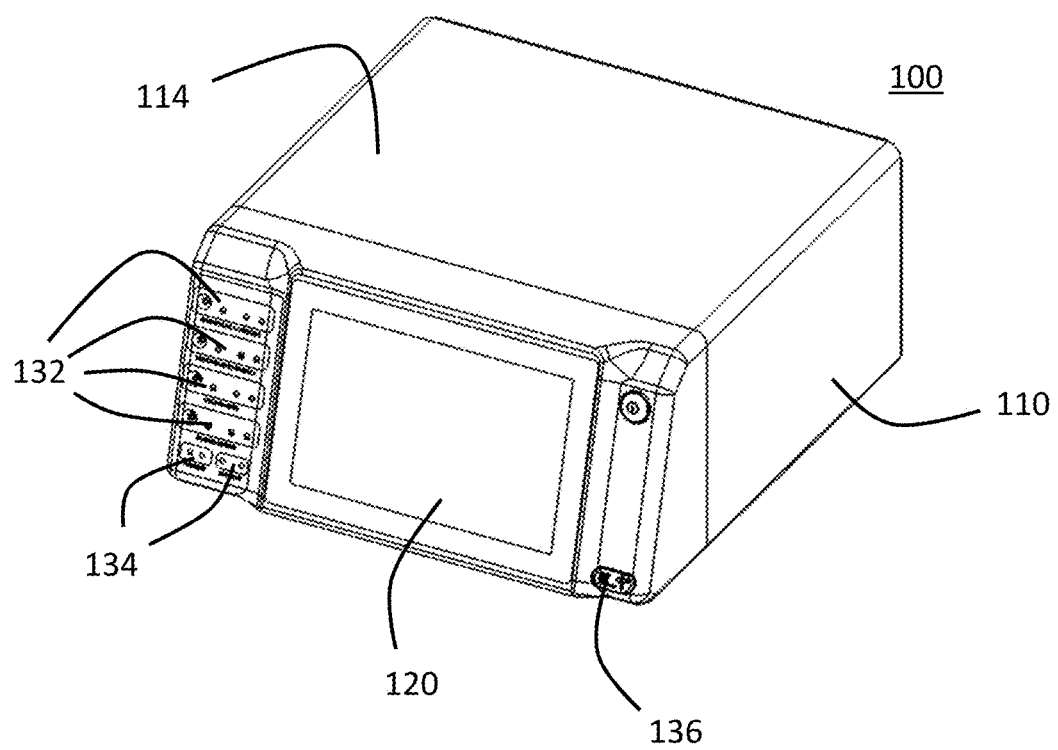
FIG. 1A is a perspective view of a preferred embodiment of a gas-enhanced electrosurgical generator.
Figure 1B:
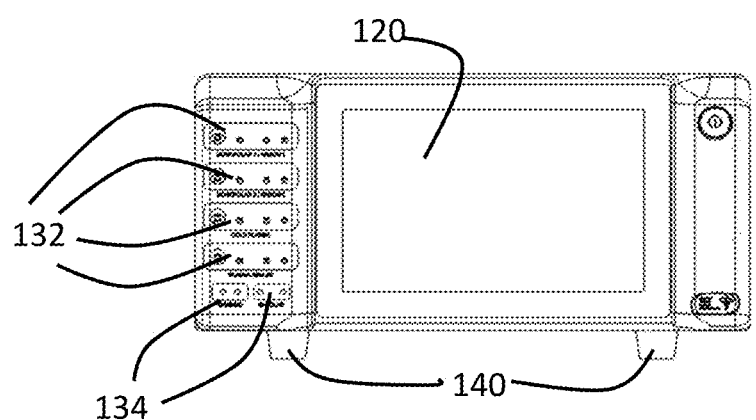
FIG. 1B is a front view of a preferred embodiment of a gas-enhanced electrosurgical generator.
Figure 1C:
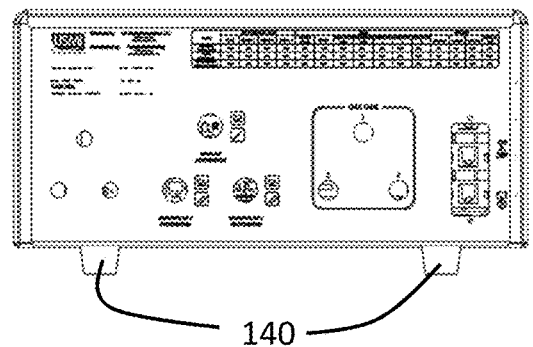
FIG. 1C is a rear view of a preferred embodiment of a gas-enhanced electrosurgical generator.
Figure 1D:
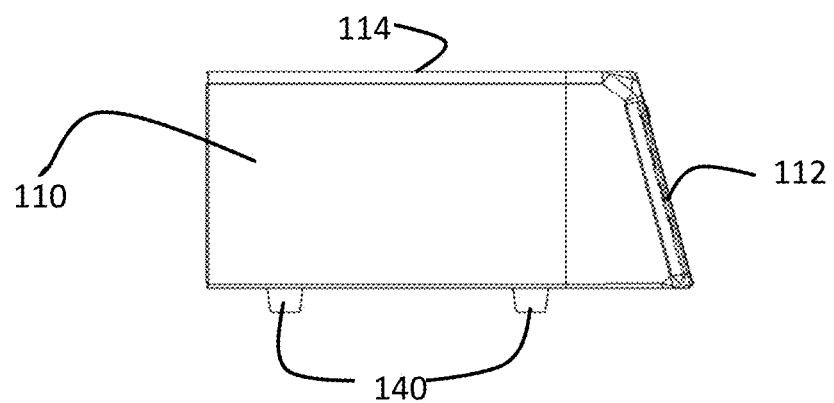
FIG. 1D is a left side view of a preferred embodiment of a gas-enhanced electrosurgical generator.
Figure 1E:
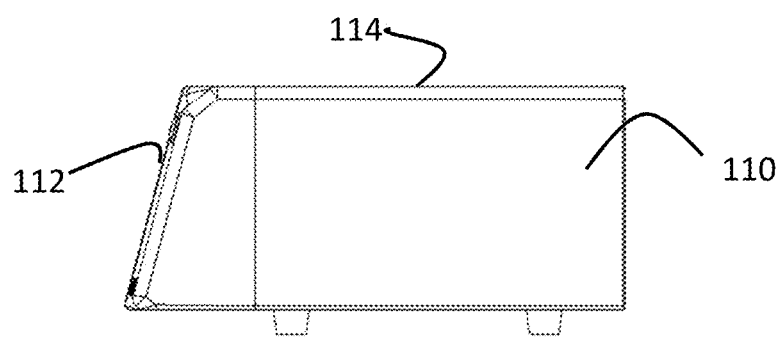
FIG. 1E is a right view of a preferred embodiment of a gas-enhanced electrosurgical generator.
Figure 2A:
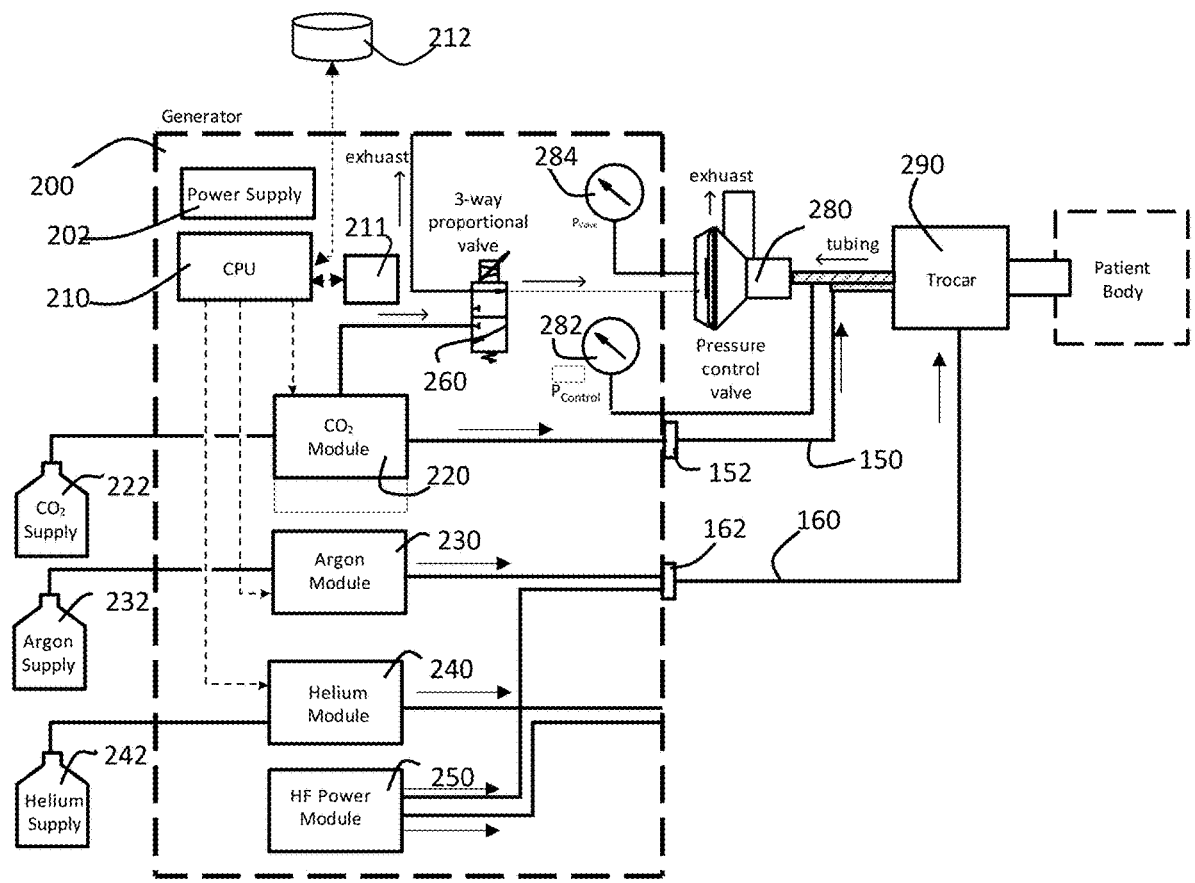
FIG. 2A is a block diagram of a preferred embodiment of a gas-enhanced electrosurgical generator having a pressure control system in accordance with the present invention configured to perform an argon-enhanced electrosurgical procedure.

One or more of the gas control modules may be mounting within a gas-enhanced electrosurgical generator 100. A gas pressure control system 200 for controlling a plurality of gas control modules 220, 230, 240 within a gas-enhanced electrosurgical generator is described with reference to FIGS. 2A-2D. A plurality of gas supplies 222, 232, 242 are connected to the gas pressure control system 200, and more specifically, to the respective gas control modules 220, 230, 240 within the gas pressure control system 200. The gas pressure control system 200 has a power supply 202 for supplying power to the various components of the system. A CPU 210 controls the gas pressure control modules 220, 230, 240 in accordance with settings or instructions entered into the system through a graphical user interface on the display 120. The system is shown with gas control modules for $CO_2$, argon and helium, but the system is not limited to those particular gases. In the embodiment shown in FIGS. 2A-2D, the $CO_2$ is shown as the gas used to insufflate an abdomen (or other area of a patient). The gas pressure control system 200 has a 3-way proportional valve connected to the gas control module 220. While FIG. 2A shows the 3-way proportional valve connected only to the CO2 control module 220, the 3-way proportional valves could be connected to a different gas control module 230 or 240. The gas pressure control system 200 further has an HF power module 250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. No. 4,040,426 and U.S. Pat. No. 4,781,175. The system further could have a converter unit for converting the HF power to a lower frequency, such as may be used for cold atmospheric plasma and is described in U.S. Patent Application Publication No. 2015/0342663.

Figure 2B:
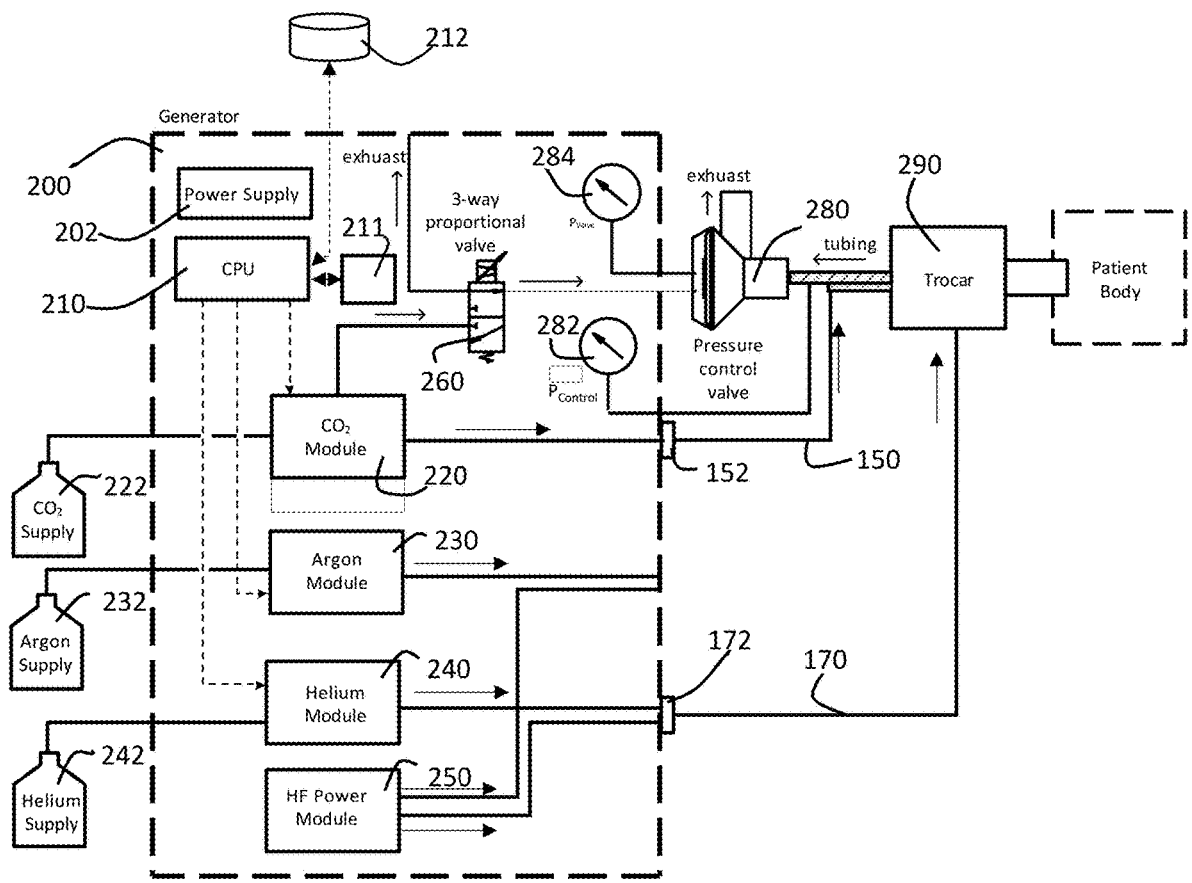
FIG. 2B is a block diagram of a preferred embodiment of a gas-enhanced electrosurgical generator having a pressure control system in accordance with the present invention configured to perform a cold atmospheric plasma procedure.
Figure 2C:
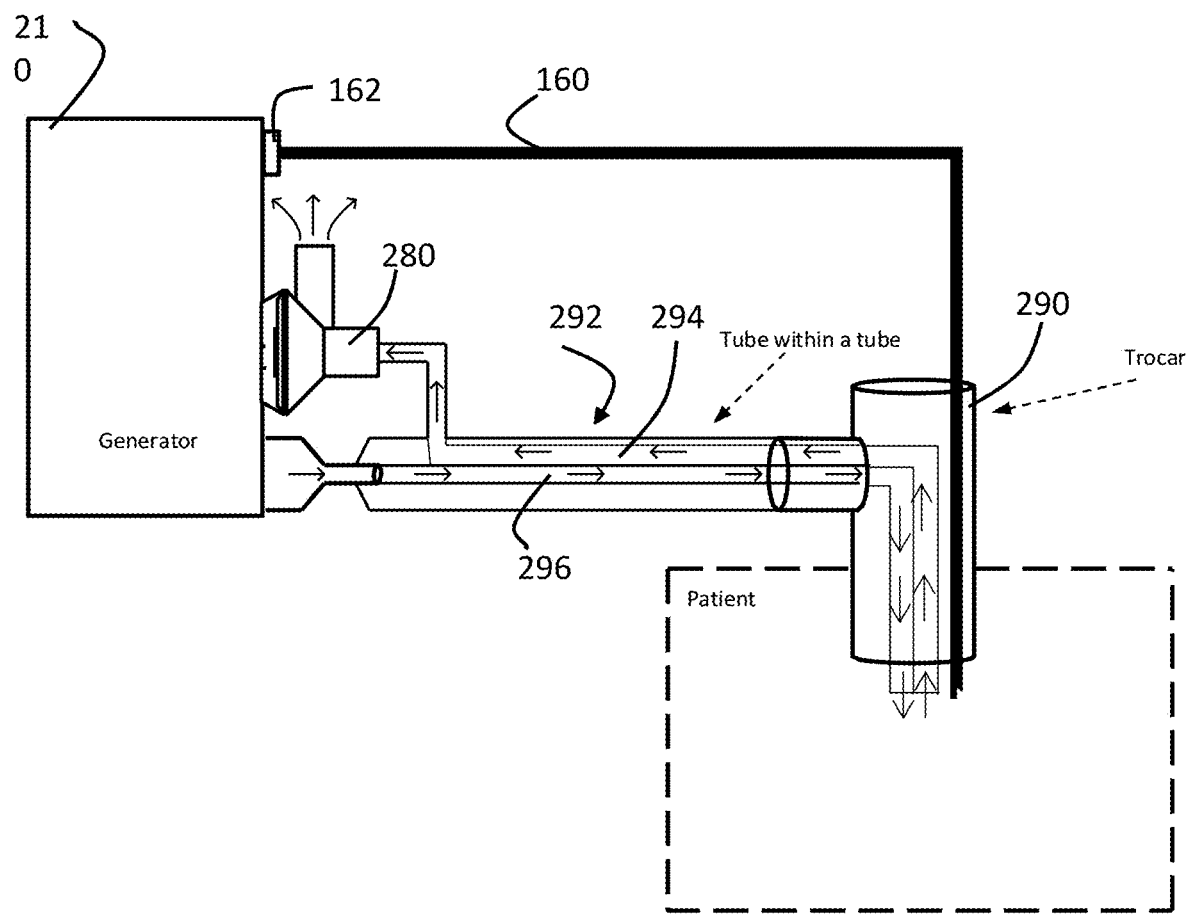
FIG. 2C is a diagram of a trocar for the embodiment of FIG. 2A in accordance with the present invention.

The outlet port of gas control module 220 is connected to a connector 136 on the generator housing. While connector 136 and the other connectors are shown on the front face of the housing 110, they could be elsewhere on the housing. The outlet ports of gas control modules 230, 240 each are connected to tubing or other channel to a connector 132. A connector 152 connects to connector 136 and is as tubing that runs to and connects to tubing 292. The tubing 292 is connected to a pressure control valve or stopcock 280 and extends into the trocar. The pressure control valve 280 is used to control pressure within the patient. The gas pressure control system further has a pressure sensor 282 connected to the tubing 292 to sense pressure in the tubing 292 and a pressure sensor 284 for sensing pressure in the pressure control valve 280. As shown in FIG. 2C, the tubing 292 is actually tube within a tube such that gas supplied from the generator travels to the trocar and patient through tube 296 and gas is released out of the patient through tube 294.

As shown in FIG. 2A the connector 132 to which control module 230 is connected has a gas-enhanced electrosurgical instrument 160 having a connector 162 connected to in. In FIG. 2A, gas control module 230 controls flow of argon gas, so the instrument 160 is an argon gas-enhanced electrosurgical tool such as an argon plasma probe such as is disclosed in U.S. Pat. No. 5,720,745, a hybrid plasma cut accessory such as is disclosed in U.S. Patent Application Publication No. 2017/0312003 or U.S. Patent Application Publication No. 2013/0296846, or a monopolar sealer such as is disclosed in U.S. Patent Application Publication No. 2016/0235462. Other types of argon surgical devices similarly can be used. As shown in FIG. 2B the connector 132 to which control module 240 is connected has a gas-enhanced electrosurgical instrument 170 having a connector 172 connected to in. In FIG. 2B, gas control module 240 controls flow of helium gas, so the instrument 170 is, for example, a cold atmospheric plasma attachment such as is disclosed in U.S. Patent Application Publication No. 2016/0095644.

The system provides for control of intraabdominal pressure in a patient. The pressure control valve 280 has a chamber within it. The pressure in that chamber is measured by pressure sensor 284. $CO_2$ is supplied to the chamber within pressure control valve 280 from gas control module 220 via 3-way proportional valve 260. Pressure in that chamber within the pressure control valve 280 also may be released via 3-way proportional valve 260. In this manner, the system can use the pressure sensor 284 and the 3-way proportional valve to achieve a desired pressure (set through a user interface) in the chamber within the pressure control valve 280. The pressure sensor 282 senses the pressure in the tubing 294 (and hence the intraabdominal pressure). The pressure control valve 280 then releases pressure through its exhaust to synchronize the intraabdominal pressure read by sensor 282 with the pressure in the chamber within the pressure control valve as read by pressure sensor 284. The readings from sensors 282, 284 can be provided to CPU 210, which in turn can control flow of $CO_2$ and one of argon and helium, depending on the procedure being performed, to achieve a stable desired intraabdominal pressure.

Figure 2D:
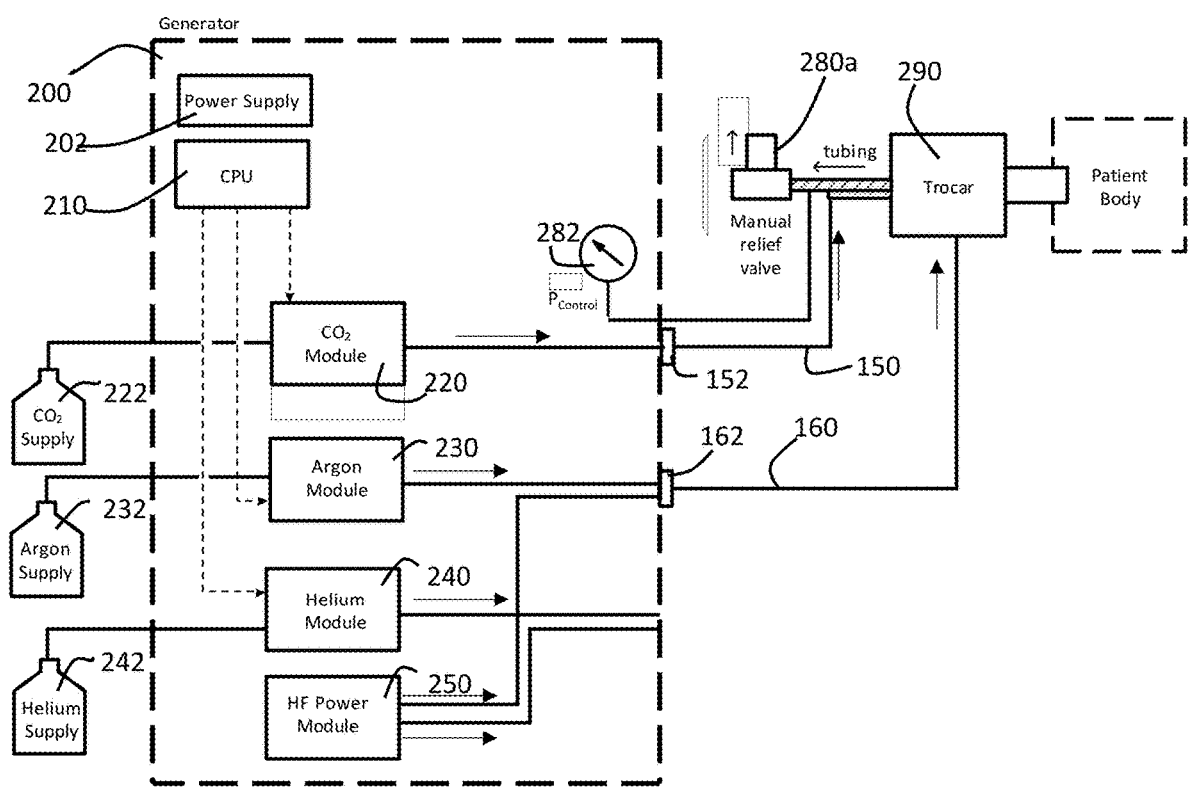
FIG. 2D is a block diagram of an alternate preferred embodiment of pressure control system of a gas-enhanced electrosurgical generator having a pressure control system in accordance with the present invention configured to perform an argon-enhanced electrosurgical procedure.

An alternative embodiment of the gas pressure control system is shown in FIG. 2D. This this system the automatic stopcock or pressure control valve 280 has been replaced by a manual relief valve 280a that is controlled or operated by the surgeon using the system.

A gas control module 300 in accordance with the present invention is designed for gas-enhanced electrosurgical systems. Conventionally, gas-enhanced electrosurgical systems have an electrosurgical generator and a gas control unit that have separate housings. The conventional gas control unit typically controls only a single gas such as argon, $CO_2$ or helium. The present invention is a gas control module 300 that may be used in a gas control unit or in a combined unit functioning both as an electrosurgical generator and as a gas control unit. Further, a plurality of gas control modules in accordance with the present invention may be combined in a single gas control unit or combination generator/gas control unit to provide control of multiple gases and provide control for multiple types of gas-enhanced surgery such as argon gas coagulation, hybrid plasma electrosurgical systems and cold atmospheric plasma systems.

Figure 3A:
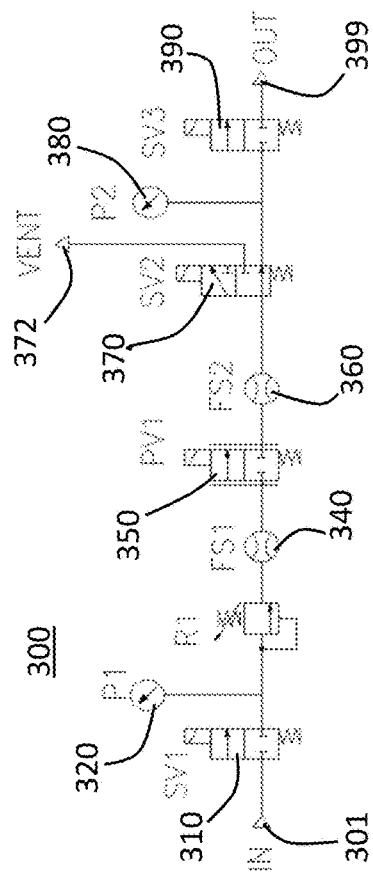
FIG. 3A is a schematic flow diagram illustrating the gas flow through the module and the method by which the module controls the gas flow in accordance with a preferred embodiment of the present invention.

FIG. 3A is a schematic flow diagram illustrating the gas flow through the gas control module 300 and the method by which the module 300 controls the gas flow in accordance with a preferred embodiment of the present invention. As shown in FIG. 3A, the gas enters the gas control module at an inlet port (IN) 301 and proceeds to first solenoid valve (SV1) 310, which is an on/off valve. In an exemplary embodiment, the gas enters the gas module at a pressure of 75 psi. The gas then proceeds to a first pressure sensor (P1) 320, to a first pressure regulator (R1) 330. In an exemplary embodiment, the first pressure regulator (R1) 330 reduces the pressor of the gas from 75 psi to 18 psi. After the pressure regulator (R1) 330, the gas proceeds to flow sensor (FS1) 340, which sense the flow rate of the gas. Next, the gas proceeds to proportional valve (PV1) 350, which permits adjustment of a percentage of the opening in the valve. The gas then proceeds to a second flow sensor (FS2) 360, which senses the flow rate of the gas. This second flow sensor (FS2) 360 provides redundancy and thus provides greater safety and accuracy in the system. Next the gas proceeds to a second solenoid valve (SV2) 370, which is a three-way valve that provides for a vent function that can allow gas to exit the module through a vent 372. The gas then proceeds to a second pressure sensor (P2) 380, which provides a redundant pressure sensing function that against produces greater safety and accuracy of the system. Finally, the gas proceeds to a third solenoid valve (SV3) 390, which is a two-way on/off valve that is normally closed and is the final output valve in the module. The gas exits the module at and output port (OUT) 399, which is connected to tubing or other channel that provides a passageway for the gas to flow to an accessory connected to the electrosurgical unit.

Figure 3B:
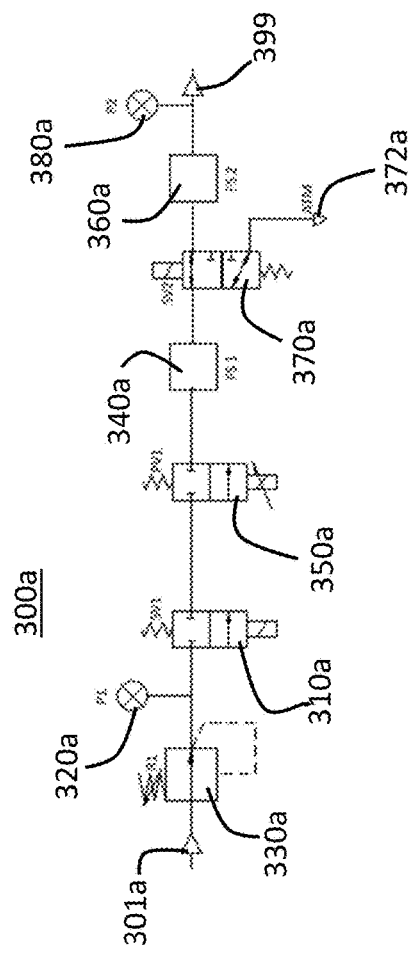
FIG. 3B is a schematic flow diagram illustrating the gas flow through an alternate embodiment of the module and the method by which the module controls the gas flow in accordance with a preferred embodiment of the present invention.

FIG. 3B is a schematic flow diagram of an alternate embodiment of a gas control module illustrating the gas flow through the gas control module 300a and the method by which the module 300a controls the gas flow in accordance with a preferred embodiment of the present invention. As shown in FIG. 3B, the gas enters the gas control module at an inlet port 301a and proceeds to a first pressure regulator (R1) 330a. In an exemplary embodiment, the first pressure regulator (R1) 330a reduces the pressor of the gas from about 50-100 psi to 15-25 psi. After the pressure regulator (R1) 330a, the gas proceeds to a first pressure sensor (P1) 320a and then to a first solenoid valve (SV1) 310a, which is an on/off valve. Next, the gas proceeds to proportional valve (PV1) 350a, which permits adjustment of a percentage of the opening in the valve. Next, the gas proceeds to flow sensor (FS1) 340a, which sense the flow rate of the gas. ext the gas proceeds to a second solenoid valve (SV2) 370a, which is a three-way valve that provides for a vent function that can allow gas to exit the module through a vent 372a. The gas then proceeds to a second flow sensor (FS2) 360a, which senses the flow rate of the gas. This second flow sensor (FS2) 360a provides redundancy and thus provides greater safety and accuracy in the system. The gas then proceeds to a second pressure sensor (P2) 380a, which provides a redundant pressure sensing function that against produces greater safety and accuracy of the system. The gas exits the module at and output port 399a, which is connected to tubing or other channel that provides a passageway for the gas to flow to an accessory connected to the electrosurgical unit.

The various valves and sensors in either embodiment of the module are electrically connected to a main PCB Board through a connector 490. The PCB connector 490 is connected to a PCB Board that has a microcontroller (such as CPU 210 in the embodiment shown in FIG. 2A). As previously noted, a plurality of gas modules can be in a single gas control unit or single electrosurgical generator to provide control of multiple differing gases. The plurality of gas control modules further may be connected to the same PCB Board, thus providing common control of the modules.

Figure 4:
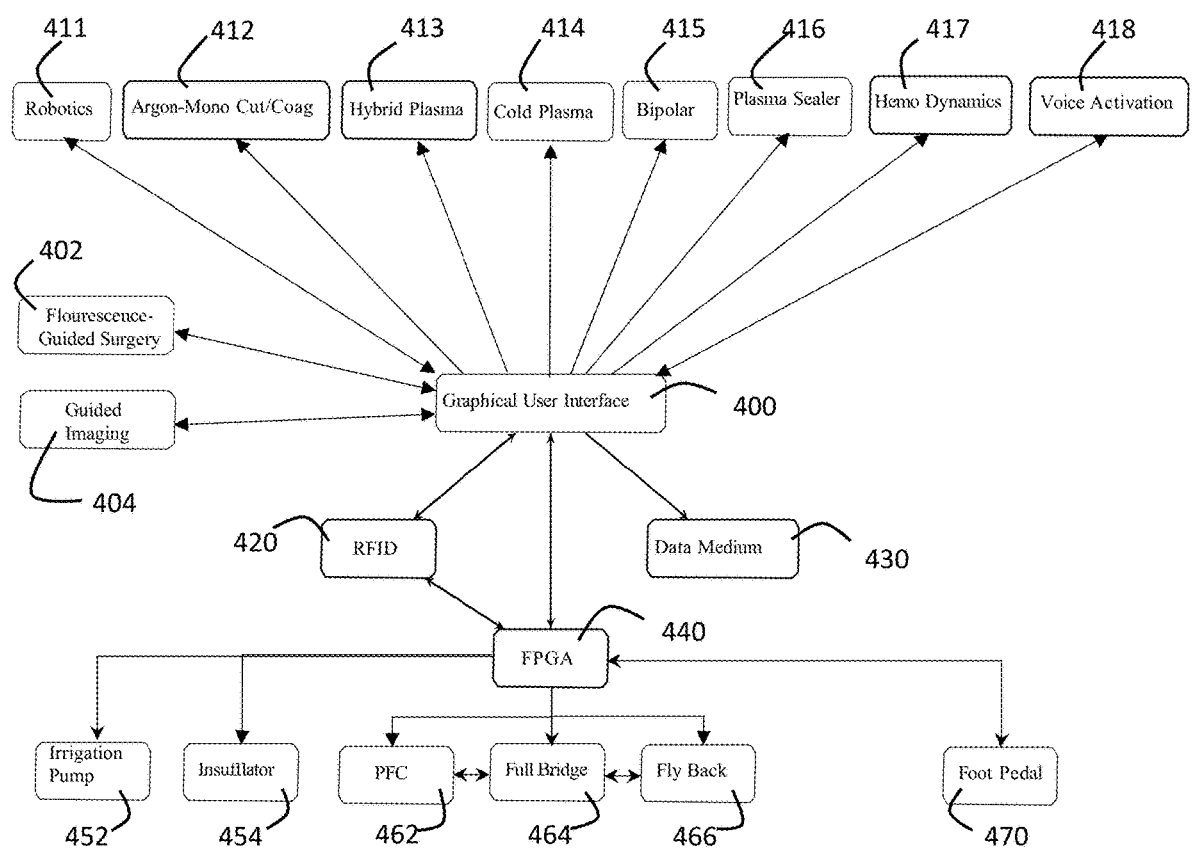
FIG. 4 is a diagram of a graphical user interface in accordance with a preferred embodiment of the present invention.

As shown in FIG. 4, the generator further may have graphical user interface 400 for controlling the components of the system using the touch screen display 120. The graphical user interface 400 for example, may control robotics 411, argon-monopolar cut/coag 412, hybrid plasma cut 413, cold atmospheric plasma 414, bipolar 415, plasma sealer 416, hemo dynamics 417 or voice activation 418. The graphical user interface further may be used with fluorescence-guided surgery 402. For example, J. Elliott, et al., "Review of fluorescence guided surgery visualization and overlay techniques," BIOMEDICAL OPTICS EXPRESS 3765 (2015), outlines five practical suggestions for display orientation, color map, transparency/alpha function, dynamic range compression and color perception check. Another example of a discussion of fluorescence-guided surgery is K. Tipirneni, et al., "Oncologic Procedures Amenable to Fluorescence-guided Surgery," Annals of Surgery, Vo. 266, No. 1, Jul. 2017). The graphical user interface (GUI) further may be used with guided imaging such as CT, MRI or ultrasound. The graphical user interface may communicate with RFID 420 (such as may be found in various electrosurgical attachments) and may collect and store usage data in a storage medium 430. The graphical user interface 400 communicates with FPGA 440, which may control irrigation pump 452, insufflator 454, PFC 462, full bridge 464 for adjusting the power output, fly back 466 for regulating the power (DC to AC) and a foot pedal 470. The GUI 400 further communicates with a database of cancer cell line data with associated predicted CAP settings or dosages via the CPU 210. The databases storage may be internal memory or other internal storage 211 or external storage 212 as shown in FIGS. 2A and 2B. The data storage 430 in FIG. 4 may be in one or both of these memories or storages 211 or 212.

Experiments for Determining Optimum CAP Settings

To develop the present invention, a Cold Atmospheric Plasma (CAP) device was tested on a wide range of cancer cell lines with different combinations of power settings, treatment times, and gas flow rate. In this way, optimal dosages for each cancer type were determined and recorded. The following test procedures were sued. To determine the effective plasma dose required to significantly reduce cell viability two flowrates were chosen; 1 L/min and 3 L/min of helium. Based on initial testing 1-5 minutes with 40-80 power, and 30-120 sec with 20-40 power, were chosen as an effective range for 3 L/min and 1 L/min, respectively. The power settings of 20P, 40P, 60P, and 80P used in this study are 5 W, 8 W, 11 W, and 15.7 W at 3 L/min. At 1 L/min of 20P and 40P, the power are 5 W and 6 W respectively. The detailed power measurement of our CAP device was conducted and reported in another paper which is currently under review.

MTT assays were used to determine the dose of CAP needed to significantly reduce cell viability. MTT assays were performed on CAP treated cancer cell lines 48 hours post treatment. The viability of the treated cells was normalized to an untreated (control) group.

Results

Reduction of Cell Viability by CAP in Malignant Solid Tumor Cell Lines

Figure 5A:
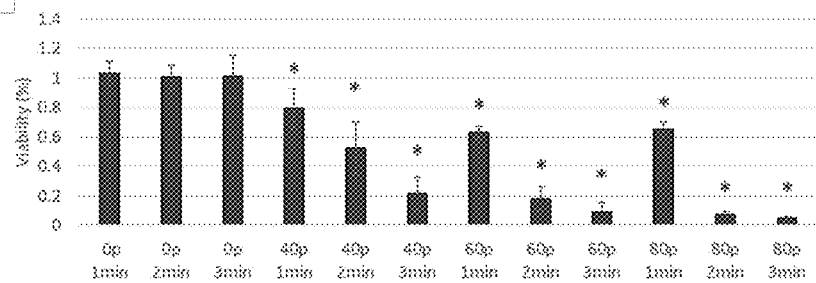
FIGS. 5A and 5B illustrate a reduction of viability of 769-P following CAP treatment. CAP treatment of 769-P significantly reduces viability at all doses tested.
Figure 5B:
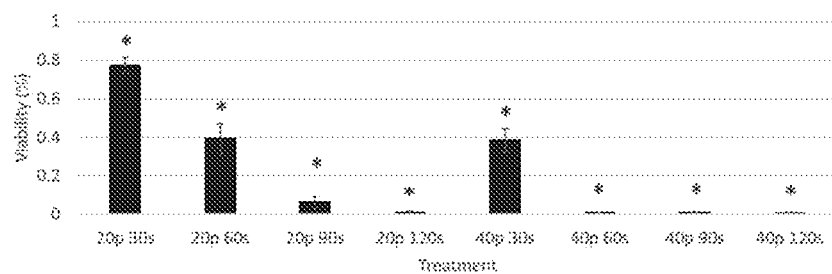
Figure 6A:
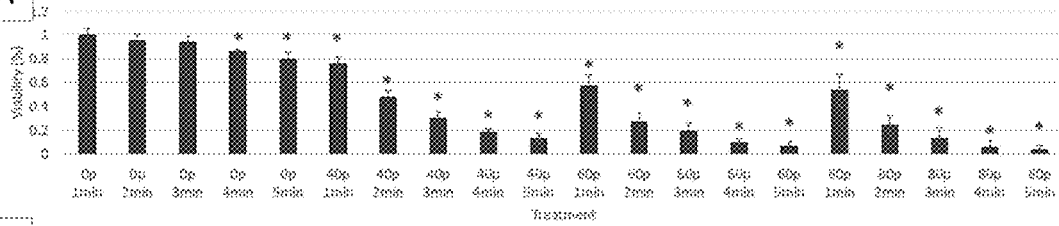
FIGS. 6A and 6B illustrate reduction of viability of HCT-116 following CAP treatment. CAP treatment of HCT-116 significantly reduces viability at all doses tested.
Figure 6B:
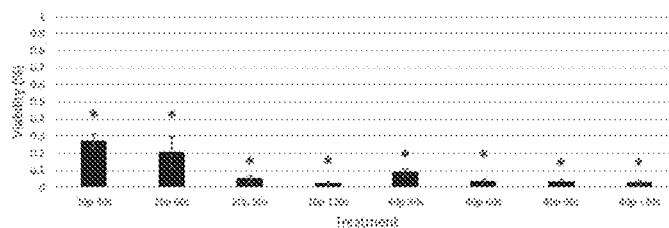
Figure 7A:
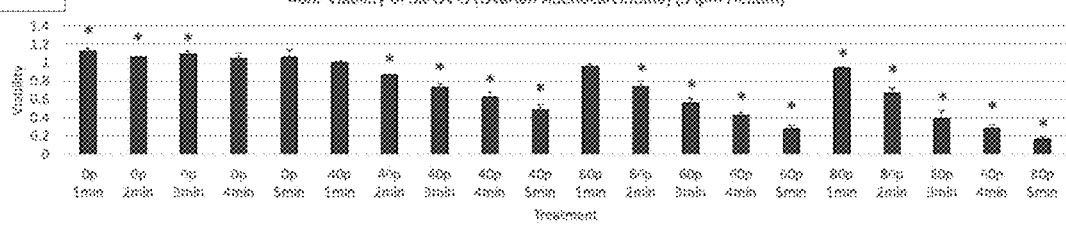
FIGS. 7A and 7B illustrates reduction of viability of SK-OV-3 following CAP treatment. CAP treatment of SK-OV-3 significantly reduces viability at nearly all doses tested using 3 L/min (FIG. 8A) and at all doses using 1 L/min flow rate (FIG. 8B).
Figure 7B:
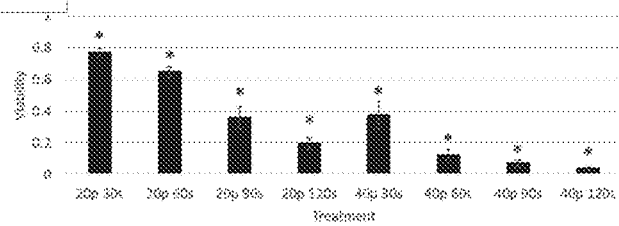
Figure 8A:
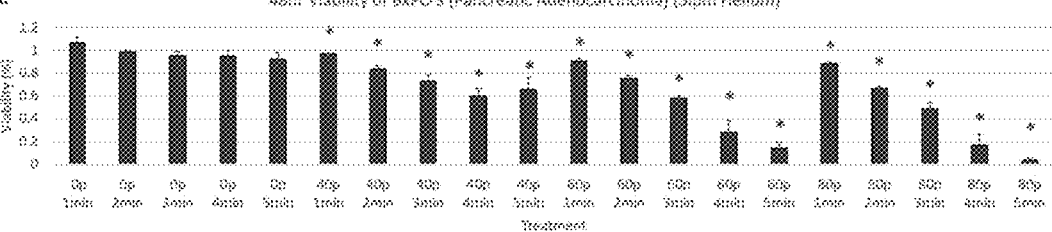
FIGS. 8A and 8B illustrates reduction of viability of BxPC-3 following CAP treatment. CAP treatment of BxPC-3 significantly reduces viability at nearly all doses tested.
Figure 8B:
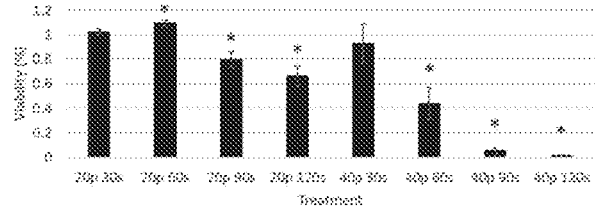

Viability of 769-P renal adenocarcinoma cells was dose-dependent and significantly reduced at all time and power combinations tested (FIGS. 5A and 5B). Helium flow alone (0W) did not significantly impact cell viability (FIG. 5A). At the highest doses using 3 L/min viability was reduced to 4.9% (P <0.001) while viability at 20P 120 seconds was <1% (P <0.001) for 1 L/min. Increasing the power to 40P did not result in a further reduction (P=0.65) (FIG. 5B). CAP was equally as effective in reducing viability in HCT-116 colorectal carcinoma cells. At 3 L/min viability was 76% at 40P 1 minute (P <0.01) and this decreased to 3.6% at the highest dose of 80P 5 minutes (P<0.001) (FIG. 6A). The decreased in viability when using 1 L/min required a lower dose. Initially, at 20P 30 seconds and 60 seconds, viability was reduced to 27% (P<0.001) and 21% (P<0.01), respectively (FIG. 6B). However, beginning at 20P 90 seconds viability was reduced to 5.0% (P<0.001) which only slightly decreased with a higher dose, the highest dose resulting in 2.6% viability (P<0.001). CAP also had a clear dose-dependent effect in the reduction of viability in ovarian adenocarcinoma cell line; SK-OV-3. At the lowest dose, using 3 L/min, viability was only reduced to 87% (P<0.001) which decreased to 17% (P<0.001) at 80P for 5 minutes (FIG. 7A). Similar results were found with the lower flow rate (FIG. 7B). 20P for 30 seconds resulted in 77% viability (P<0.001) which decreased to 4% viability (P<0.0001) at 40P for 120 seconds. BxPC-3 (pancreatic adenocarcinoma) required a higher dose to effectively reduce viability (FIG. 8A). At 60P and 5 minutes and 80P for 5 minutes viability was reduced to 14% (P<0.0001) and 4% (P<0.0001), respectively. The low flow rate treatment showed a similar pattern requiring a higher dose to reduce viability. At 40P for 90 seconds and 40P for 120 seconds the viability was reduced to 5% (P<0.0001) and 1% (P<0.0001), respectively (FIG. 8B). Esophageal adenocarcinoma cell line, OE33, also required a higher dose to decrease viability below 20%. Using the high flow rate at 80P for 5 minutes viability was reduced to 16% (P<0.001) (FIG. 9A). At 1 L/min an 40P for 120 seconds viability was reduced to 15% (P<0.0001) (FIG. 9B). Taken together, this data demonstrates that CAP reduced cell viability in a time- and power-dependent manner in all cell lines tested.

Discussion

This present work represents the first effort to describe the dose-dependent reduction of viability, as a combination of treatment time and power settings, on multiple malignant solid tumor cell lines using a CAP system. This CAP does not induce any damage on normal tissue. CAP treatment consistently resulted in a dose-dependent reduction in viability on all solid tumor cell lines tested. While the lowest effective dose varied from cell line to cell line, in each case an 80-99% reduction in viability was achievable 48 hours after CAP treatment. 769-P and HCT-116 required a lower dose of plasma while SK-OV-3, BxPC-3, and OE33 required a relatively higher dose. In all cell lines tested, helium treatment alone (OP) showed no decrease in viability, indicating that the observed effects are due to CAP. While in several of the cell lines 1 L/min flow rate resulted in a lower viability at a lower dose, this cannot be directly compared with the 3 L/min results. This is because the beam length, media volume, and cell number are different between these two assays. Xu and Dai et al. have suggested a formula to compare plasma dose among treatment conditions within one cell type and this may be necessary to compare future result. See, Xu, X.; Dai, X.; Xiang, L.; Cai, D.; Xiao, S.; Ostrikov, K., "Quantitative assessment of cold atmospheric plasma anti-cancer efficacy in triple-negative breast cancers," *Plasma Processes and Polymers* 2018.

Ma et al. demonstrated that the effectiveness of non-thermal plasma treatment was partially dependent on p53 expression [13]. The viability of cancer cells lacking p53 was significantly reduced by non-thermal plasma treatment while p53+ cells were less affected. It is thought that this is due to the role of p53 in protecting the cell from reactive oxygen species. See, Sablina, A. A.; Budanov, A. V.; Ilyinskaya, G. V.; Agapova, L. S.; Kravchenko, J. E.; Chumakov, P. M., "The antioxidant function of the p53 tumor suppressor," *Nat Med* 2005, 11, 1306-1313. However, based on established literature, the cell lines tested here, except for SK-OV-3, have been shown to be positive for p53 (Table 1, below).

For 769-P see Wang, J.; Zhang, P.; Zhong, J.; Tan, M.; Ge, J.; Tao, L.; Li, Y. Zhu, Y.; Wu, L.; Qiu, J., et al., "The platelet isoform of phosphofructokinase contributes to metabolic reprogramming and maintains cell proliferation in clear cell renal cell carcinoma," *Oncotarget* 2016, 7, 27142-27157; Miyazaki, J.; Ito, K.; Fujita, T.; Matsuzaki, Y.; Asano, T.; Hayakawa, M.; Asano, T.; Kawakami, Y., "Progression of human renal cell carcinoma via inhibition of rhoa-rock axis by parg1," *Transl Oncol* 2017, 10, 142-152; Mu, W.; Hu, C.; Zhang, H.; Qu, Z.; Cen, J.; Qiu, Z.; Li, C.; Ren, H.; Li, Y.; He, X., et al., "Mir-27b synergizes with anticancer drugs via p53 activation and cyp1b1 suppression," *Cell Res* 2015, 25, 477-495; and Bamford, S.; Dawson, E.; Forbes, S.; Clements, J.; Pettett, R.; Dogan, A.; Flanagan, A.; Teague, J.; Futreal, P. A.; Stratton, M.R., et al., "The cosmic (catalogue of somatic mutations in cancer) database and website," *Br J Cancer* 2004, 91, 355-358.

For HCT-116 see Ma, Y.; Ha, C. S.; Hwang, S. W.; Lee, H. J.; Kim, G. C.; Lee, K. W.; Song, K., "Non-thermal atmospheric pressure plasma preferentially induces apoptosis in p53-mutated cancer cells by activating ros stress-response pathways," *PLoS One* 2014, 9, e91947 and O'Connor, P. M.; Jackman, J.; Bae, I.; Myers, T. G.; Fan, S.; Mutoh, M.; Scudiero, D. A.; Monks, A.; Sausville, E. A.; Weinstein, J. N., et al., "Characterization of the p53 tumor suppressor pathway in cell lines of the national cancer institute anticancer drug screen and correlations with the growth-inhibitory potency of 123 anticancer agents," *Cancer Res* 1997, 57, 4285-4300.

For SK-OV-3, see Bamford, S.; Dawson, E.; Forbes, S.; Clements, J.; Pettett, R.; Dogan, A.; Flanagan, A.; Teague, J.; Futreal, P. A.; Stratton, M. R., et al., "The cosmic (catalogue of somatic mutations in cancer) database and website," *Br J Cancer* 2004, 91, 355-358; O'Connor, P. M.; Jackman, J.; Bae, I.; Myers, T. G.; Fan, S.; Mutoh, M.; Scudiero, D. A.; Monks, A.; Sausville, E. A.; Weinstein, J. N., et al., "Characterization of the p53 tumor suppressor pathway in cell lines of the national cancer institute anticancer drug screen and correlations with the growth-inhibitory potency of 123 anticancer agents," *Cancer Res* 1997, 57, 4285-4300; Antoun, S., Atallah, D., Tahtouh, R., Alaaeddine, N., Moubarak, M., Khaddage, A., Ayoub, E. N., Chahine, G., and Hilal, G., "Different tp53 mutants in p53 overexpressed epithelial ovarian carcinoma can be associated both with altered and unaltered glycolytic and apoptotic profiles," *Cancer Cell Int* 2018, 18, 14; and Yaginuma, Y.; Westphal, H., "Abnormal structure and expression of the p53 gene in human ovarian carcinoma cell lines," *Cancer Res* 1992, 52, 4196-4199

For BxPC-3, see Chen, D.; Niu, M.; Jiao, X.; Zhang, K.; Liang, J.; Zhang, D., "Inhibition of akt2 enhances sensitivity to gemcitabine via regulating puma and nf-kappab signaling pathway in human pancreatic ductal adenocarcinoma," *Int J Mol Sci* 2012, 13, 1186-1208; Wang, F.; Li, H.; Yan, X. G.; Zhou, Z. W.; Yi, Z. G.; He, Z. X.; Pan, S. T.; Yang, Y. X.; Wang, Z. Z.; Zhang, X., et al., "Alisertib induces cell cycle arrest and autophagy and suppresses epithelial-to-mesenchymal transition involving pi3k/akt/mtor and sirtuin 1-mediated signaling pathways in human pancreatic cancer cells," *Drug Des Devel Ther* 2015, 9, 575-601; and Ruggeri, B.; Zhang, S. Y.; Caamano, J.; DiRado, M.; Flynn, S. D.; Klein-Szanto, A. J. "Human pancreatic carcinomas and cell lines reveal frequent and multiple alterations in the p53 and rb-1 tumor-suppressor genes," *Oncogene* 1992, 7, 1503-1511.

For OE33, see, Bamford, S.; Dawson, E.; Forbes, S.; Clements, J.; Pettett, R.; Dogan, A.; Flanagan, A.; Teague, J.; Futreal, P. A.; Stratton, M. R., et al., "The cosmic (catalogue of somatic mutations in cancer) database and website," *Br J Cancer* 2004, 91, 355-358 and Liu, D. S.; Read, M.; Cullinane, C.; Azar, W. J.; Fennell, C. M.; Montgomery, K. G.; Haupt, S.; Haupt, Y.; Wiman, K. G.; Duong, C. P., et al., "Apr-246 potently inhibits tumour growth and overcomes chemoresistance in preclinical models of oesophageal adenocarcinoma," *Gut* 2015, 64, 1506-1516.

TABLE 1

Status and expression of p53 in all cell types tested; wild-type (WT), mutant (MUT).

| Cell Name | Cell Type | p53 Status | P53 Expression |
|---|---|---|---|
| 769-P | Renal adenocarcinoma | WT | Positive |
| HCT-116 | Colorectal carcinoma | WT | Positive |

TABLE 1-continued

Status and expression of p53 in all cell types
tested; wild-type (WT), mutant (MUT).

| Cell Name | Cell Type | p53 Status | P53 Expression |
|---|---|---|---|
| SK-OV-3 | Ovarian adenocarcinoma | MUT/NULL | Negative |
| BxPC-3 | Pancreatic adenocarcinoma | MUT | Positive |
| OE33 | Esophageal adenocarcinoma | MUT | Positive |

Ma et al. also used HCT-116 and surprisingly found only a slight reduction in viability whereas we found that viability was reduced to as low as 3.6% (FIG. 6A). This is likely due to differences in plasma generation, flow rate, and assay timing. The cell lines tested here also include both wild-type (WT) and mutant p53 (Table 1). Despite positive p53 expression, or status, the viability of these cell types was significantly affected by CAP treatment. However, the cell lines with wild-type p53 (769-P/FIGS. 5A and 5B, HCT-116/FIGS. 6A and 6B) tended to require a lower dose of CAP to reduce viability compared to those with mutant p53 (BxPC-3/FIGS. 4A and 4B, OE33/FIGS. 9A and 9B).

Further experiments will investigate the effect of CAP on additional cell lines as well as the potential of combined therapies. For cell lines that require a higher dose of CAP to effectively reduce viability; that dose may be reduced with the addition of chemotherapy drugs. Combination therapy may also further reduce viability when combined with CAP. This would match the approach taken in a surgical setting and could lead to improved patient outcomes.

Materials and Methods

Cold Plasma Device

Cold atmospheric plasma (CAP) was generated using a USMI SS-601 MCa high-frequency electrosurgical generator integrated with a USMI Cold Plasma Conversion Unit and connected to a Canady Helios Cold Plasma Scalpel. Helium flow was set to a constant 1 L/min and 20P or 40P or 3 L/min and power set to 40P, 60P, or 80P. The plasma scalpel was placed such that the tip of the scalpel was 1.5 cm (at 1 L/min) or 2 cm (at 3 L/min) from the surface of the cell media and was not moved during treatment (FIGS. 10A and 10B).

Cell Culture

BxPC-3 pancreatic adenocarcinoma and 769-P renal adenocarcinoma were purchased from ATCC (Manassas, Va.). OE33 esophageal adenocarcinoma was purchased from Sigma-Aldrich (St. Louis, Mo.). HCT-116 colorectal carcinoma and SK-OV-3 ovarian adenocarcinoma were generously donated by The George Washington University. All cell lines were maintained with required culture media according to the supplier protocol. When cells reached approximately 80% confluence, cells were seeded at a concentration of $5 \times 10^3$ or $10^5$ cells/well into 96-well or 12-well plates (USA Scientific, Ocala, Fla.), respectively, for cell viability assays. For BxPC-3 $\times 10^4$ cells were required for the 96-well assay.

Cell Viability Assay

Thiazolyl Blue Tetrazolium Bromide (MTT) assay was performed on the cells 48 hours after plasma treatment following the manufacturer's protocol. Briefly, cells were incubated with MTT at a concentration of 0.5 mg/ml after 48 hours post treatment for 3 hours in a 37° C. and 5% $CO_2$ humidified incubator. Then, MT each well to dissolve the formazan crystals. All the MTT assay reagents were purchased from Sigma-Aldrich (St. Louis, Mo). The absorbance of the dissolved compound was measured by BioTek Synergy HTX (Winooski, Vt.) microplate reader at 570 nm.

Statistics

All viability assays were repeated for at least 3 times with 2 replicates each. Data was plotted by Microsoft Excel 2016 as mean±standard error of the mean. Student t-test or one-way analysis of variance (ANOVA) were used to check statistical significance where applicable. Differences were considered statistically significant for $*p \leq 0.05$.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A system for performing cold atmospheric plasma treatment on target tissue comprising:
    an RF energy source;
    a low frequency conversion unit;
    a gas control device configured to control flow of a gas;
    a processor configured to control said RF energy source, said low frequency conversion unit and said gas control device to apply energy from said low frequency conversion unit to gas flowing from said gas control module to generate reactive species that attack cancer cells but do not damage healthy cells;
    a display;
    a graphical user interface displayed on said display for controlling cold atmospheric plasma procedures;
    a data storage unit; and
    a database stored in said data storage unit, said database comprising cell line identifying data and cold atmospheric plasma settings associated with the cell line identifying data;
    wherein, the graphical user interface has input means for a surgeon to enter cell line identifier data and in response to the entry of cell line identifier data the processor is configured to automatically access the database in said data storage and adopt cold atmospheric plasma settings associated with the entered cell line identifier data in said database and display the adopted cold atmospheric plasma settings on the display.

2. A system for performing cold atmospheric plasma treatment on target tissue according to claim 1, wherein the RF energy source is a monopolar electrosurgical generator.

3. A system for performing cold atmospheric plasma treatment on target tissue according to claim 1, wherein the RF energy source, gas control device and conversion unit are modules within an integrated cold atmospheric plasma generator.

4. A system for performing cold atmospheric plasma treatment on target tissue according to claim 3, wherein said processor is in said integrated cold atmospheric plasma generator.

5. A system for performing cold atmospheric plasma treatment on target tissue according to claim 4, wherein said data storage unit is in said integrated cold atmospheric plasma generator.

6. A system for performing cold atmospheric plasma treatment on target tissue according to claim 1, wherein said display comprises a touchscreen.

7. A system for performing cold atmospheric plasma treatment on target tissue according to claim 6, wherein said touchscreen comprises a tablet computer.

8. A system for performing cold atmospheric plasma treatment on target tissue according to claim 3, wherein said data storage is external to said integrated cold atmospheric plasma generator.

9. A system for performing cold atmospheric plasma treatment on target tissue according to claim 1, wherein said data storage comprises memory in said processor.

10. A system for performing cold atmospheric plasma treatment on target tissue according to claim 1, wherein cold atmospheric plasma settings comprise at least two of power, frequency, flow rate and time.

11. An electrosurgical generator for performing cold atmospheric plasma treatment on target tissue comprising:
an RF energy module;
a gas control module configured to control flow of a gas;
a processor configured to control said RF energy module and said gas control module to apply energy from said RF energy module to gas flowing from said gas control module to generate reactive species that attack cancer cells but do not damage healthy cells;
a display;
a graphical user interface displayed on said display for controlling cold atmospheric plasma procedures;
a data storage unit; and
a database stored in said data storage unit, said database comprising cell line identifying data and cold atmospheric plasma settings associated with the cell line identifying data;
wherein, the graphical user interface has input means configured to receive cell line identifier data and in response to receipt of cell line identifier data the processor is configured to automatically access the database in said data storage or memory and adopt cold atmospheric plasma settings associated with the entered cell line identifier data in said database and display the adopted cold atmospheric plasma settings on the display.

* * * * *